United States Patent
Cho et al.

(10) Patent No.: US 10,215,680 B2
(45) Date of Patent: Feb. 26, 2019

(54) DUST MEASURING APPARATUS AND MOBILE TERMINAL FOR CONTROLLING THE SAME

(71) Applicant: LG ELECTRONICS INC., Seoul (KR)

(72) Inventors: Yongho Cho, Seoul (KR); Bolam Kim, Seoul (KR); Seonghong Park, Seoul (KR); Sangkeun Lee, Seoul (KR); Pilwon Jeong, Seoul (KR)

(73) Assignee: LG Electronics Inc., Seoul (KR)

( * ) Notice: Subject to any disclaimer, the term of this patent is extended or adjusted under 35 U.S.C. 154(b) by 0 days.

(21) Appl. No.: 15/651,598

(22) Filed: Jul. 17, 2017

(65) Prior Publication Data
US 2018/0024037 A1  Jan. 25, 2018

(30) Foreign Application Priority Data
Jul. 20, 2016  (KR) .................. 10-2016-0091976

(51) Int. Cl.
*G01N 21/00*  (2006.01)
*G01N 15/06*  (2006.01)
(Continued)

(52) U.S. Cl.
CPC ......... *G01N 15/06* (2013.01); *G01N 15/1429* (2013.01); *G01N 15/1459* (2013.01);
(Continued)

(58) Field of Classification Search
CPC .................. G01N 21/53; G01N 15/06; G01N 2015/0693; G01N 2021/473;
(Continued)

(56) References Cited

U.S. PATENT DOCUMENTS

| 2004/0188598 A1* | 9/2004 | Kawai | G01N 21/53 250/222.2 |
| 2012/0154172 A1* | 6/2012 | O'Hara | H04Q 9/00 340/870.02 |
| 2014/0152986 A1 | 6/2014 | Trainer | |

FOREIGN PATENT DOCUMENTS

| JP | 06226026 | 8/1994 |
| JP | 2008267974 | 11/2008 |

(Continued)

OTHER PUBLICATIONS

International Search Report and Written Opinion in International Application No. PCT/KR2017/007287, dated Oct. 23, 2017, 14 pages (with English translation).

*Primary Examiner* — Isiaka Akanbi
(74) *Attorney, Agent, or Firm* — Fish & Richardson P.C.

(57) ABSTRACT

Disclosed herein are a dust measuring apparatus and a mobile terminal for controlling the same. The dust measuring apparatus includes a flow channel defining unit for defining a flow channel allowing a fluid containing dust to move through, a light emitter for emitting light into the flow channel, a light detector for detecting light scattered from the dust in the flow channel and converting the same into an electrical signal, and a controller for controlling the flow channel defining unit, the light emitter and the light detector. The controller is configured to verify whether a detection value received from the light detector is within an effective measurement range, vary the effective measurement range when the detection value is outside the effective measurement range, and measure, when the detection value is within the varied effective measurement range, a dust concentration based on the detection value.

19 Claims, 23 Drawing Sheets

(51) Int. Cl.
*G01N 15/14* (2006.01)
*G01N 15/00* (2006.01)

(52) U.S. Cl.
CPC ............... *G01N 2015/0046* (2013.01); *G01N 2015/0693* (2013.01)

(58) Field of Classification Search
CPC .......... G01N 15/0211; G01N 15/1459; G01N 2201/12; G01N 2015/1493; G01N 2201/068; G01N 2201/06113; G01N 21/0303; G01N 2015/1497
USPC .................... 356/335–336, 343, 338, 438–9
See application file for complete search history.

(56) References Cited

FOREIGN PATENT DOCUMENTS

| | | |
|---|---|---|
| KR | 10-2015-0070692 | 6/2015 |
| KR | 20150070692 A * | 6/2015 |
| KR | 10-2016-0014163 | 2/2016 |

\* cited by examiner

DUST MEASURING APPARATUS AND MOBILE TERMINAL FOR CONTROLLING THE SAME

This application claims priority under 35 U.S.C. § 119 to Korean Application No. 10-2016-0091976, filed on Jul. 20, 2016 which is hereby incorporated in its entirety by reference as if fully set forth herein.

BACKGROUND OF THE INVENTION

Field of the Invention

The present invention relates to a dust measuring apparatus capable of measuring a dust concentration in a flow channel and a mobile terminal for controlling the same.

Discussion of the Related Art

Recently, the frequency of exposure to fine dust emitted from automobiles and factories has increased and the hazard of fine dust to human bodies is well known.

In such situation, various apparatuses for measuring fine dust have been developed with increase of interest in health.

A dust measuring apparatus may include a light emitter for emitting light, a flow channel defining unit for defining a flow channel through which dust passes, and a light detector for detecting light scattered from the dust. The dust measuring apparatus may detect dust only when the dust is present in a common area shared by a flow channel region, light emission region and light detection region.

However, the conventional dust measuring apparatus has a limited range of measurable dust concentrations. Accordingly, if a dust concentration is beyond the limited range of dust concentrations, the conventional dust measuring apparatus may cause an error in detecting a dust concentration. Thereby, reliability of the conventional dust measuring apparatus may be lowered.

That is, if the dust concentration is below a reference concentration range, the strength of a detected signal may be too low, and thus measurement precision for the low-concentration dust may be lowered.

In addition, if the dust concentration is above the reference concentration range, the strength of a detected signal may be too high, and thus measurement precision for the high-concentration dust may be lowered.

Accordingly, there is a need for a dust measuring apparatus capable of enhancing measurement precision for low-concentration dust and high-concentration dust by widening the range of measurable dust concentrations.

SUMMARY OF THE INVENTION

Accordingly, the present invention is directed to a dust measuring apparatus and a mobile terminal for controlling the same that substantially obviate one or more problems due to limitations and disadvantages of the related art.

An object of the present invention is to solve the above and other problems. Another object of the present invention is to provide a dust measuring apparatus capable of widening the measurement range of dust concentrations by varying the effective measurement range within which dust measurement is possible, and a mobile terminal for controlling the same.

Another object of the present invention is to provide a dust measuring apparatus capable of simplifying a circuit configuration by varying the impedance of a signal received from a light detector in varying the effective measurement range, and a mobile terminal for controlling the same.

Another object of the present invention is to provide a dust measuring apparatus capable of increasing measurement precision by varying the effective measurement range according to a plurality of predetermined variation levels, and a mobile terminal for controlling the same.

Another object of the present invention is to provide a dust measuring apparatus capable of enhancing reliability of dust concentration measurement by setting a high-concentration measurement range and low-concentration measurement range which are adjacent to an effective measurement range such that the high-concentration measurement range and low-concentration measurement range partially overlap the effective measurement range, and a mobile terminal for controlling the same.

Another object of the present invention is to provide a dust measuring apparatus capable of widening the measurement range of dust concentrations by widening or narrowing the effective measurement range according to an amplification rate of a signal received from a light detector, and a mobile terminal for controlling the same.

Another object of the present invention is to provide a dust measuring apparatus capable of increasing measurement precision by readjusting the effective measurement range according to detection range performance of a light detector, and a mobile terminal for controlling the same.

Another object of the present invention is to provide a dust measuring apparatus capable of providing user convenience by transmitting, to an external terminal, dust concentration information and guide information for guiding adjustment of an effective measurement range, and a mobile terminal for controlling the same.

Another object of the present invention is to provide a dust measuring apparatus that provides a setting window for setting an effective measurement range of the dust measuring apparatus such that a user may easily and simply control the dust measuring apparatus by manually varying the effective measurement range, and a mobile terminal for controlling the same.

Another object of the present invention is to provide a dust measuring apparatus capable of improving user convenience by providing guide information for guiding ventilation by collecting environment information about a current position of the dust measurement apparatus, and a mobile terminal for controlling the same.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, a dust measuring apparatus includes a flow channel defining unit for defining a flow channel allowing a fluid containing dust to move therethrough, a light emitter for emitting light into the floor channel, a light detector for detecting light scattered from the dust in the flow channel and converting the same into an electrical signal, and a controller for controlling the flow channel defining unit, the light emitter and the light detector, wherein the controller is configured to check if a detection value received from the light detector is within an effective measurement range, vary the effective measurement range when the detection value is outside the effective measurement range, and measure, when the detection value is within the varied effective measurement range, a concentration of the dust based on the detection value.

In another aspect of the present invention, there is provided a mobile terminal for controlling a dust measuring apparatus for varying an effective measurement range enabling measurement of dust concentrations, the mobile terminal including an input unit for receiving a user input, a communication unit for establishing communication with the dust measuring apparatus, a display unit for displaying a setting window for setting an effective measurement range for the dust measuring apparatus, and a controller for controlling the input unit, the communication unit and the display unit, wherein the controller is configured to establish the communication with the dust measuring apparatus when the user input is a control mode of the dust measuring apparatus, display, when the communication is established, a setting window for setting the effective measurement range for the communication-connected dust measuring apparatus, and transmit, when the effective measurement range is set in the setting window, a control signal corresponding to the set effective measurement range to the dust measuring apparatus.

It is to be understood that both the foregoing general description and the following detailed description of the present invention are exemplary and explanatory and are intended to provide further explanation of the invention as claimed.

BRIEF DESCRIPTION OF THE DRAWINGS

Arrangements and embodiments may be described in detail with reference to the following drawings in which like reference numerals refer to like elements and wherein.

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts. As used herein, the suffixes "module" and "unit" are added or used interchangeably simply to facilitate preparation of this specification and are not intended to suggest unique meanings or functions. In describing embodiments disclosed in this specification, relevant well-known technologies may not be described in detail in order not to obscure the subject matter of the present invention. In addition, the accompanying drawings are merely intended to facilitate understanding of the embodiments disclosed in this specification and not to restrict the technical spirit of the present invention. In addition, the accompanying drawings should be understood as covering all equivalents or substitutions within the scope of the present invention.

Terms including ordinal numbers such as first, second, etc. may be used to explain various elements. However, it will be appreciated that the elements are not limited to such terms. These terms are merely used to distinguish one element from another.

When one constituent is said to be "connected" or "linked" to another, it should be understood that this means that the one constituent may be directly connected or linked to another one or another constituent may be interposed between the constituents. On the other hand, when one constituent is said to be "directly connected" or "directly linked" to another, it should be understood that this means no other constituent is interposed between the constituents.

Singular nouns encompass the plural forms thereof unless context clearly indicates otherwise.

Terms used in this specification are merely adopted to explain specific embodiments, and are not intended to limit the present invention. A singular expression includes a plural expression unless the two expressions are contextually different from each other. In this specification, terms such as "includes" or "has" are intended to indicate that characteristics, figures, steps, operations, constituents, and components disclosed in the specification or combinations thereof exist. The terms "includes" or "has" should be understood as not precluding possibility of existence or addition of one or more other characteristics, figures, steps, operations, constituents, components, or combinations thereof.

Figure 1:
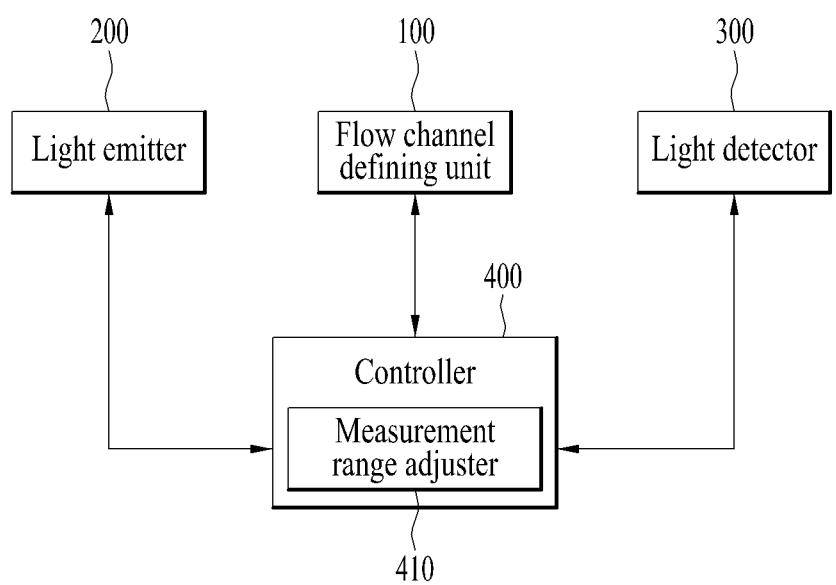
FIG. 1 is a block diagram illustrating a dust measuring apparatus according to an embodiment of the present invention.

FIG. 1 is a block diagram illustrating a dust measuring apparatus according to an embodiment of the present invention.

As shown in FIG. 1, a dust measuring apparatus 1000 may include a flow channel defining unit 100, a light emitter 200, a light detector 300, and a controller 400.

The flow channel defining unit 100 may define a flow channel through which a fluid containing dust moves. Herein, the flow channel defining unit 100 may be disposed at various positions in the apparatus where the flow channel may be defined. In addition, the flow channel defining unit 100 may form a negative pressure in the flow channel, and adjust the magnitude of the negative pressure according to the control signal of the controller 400 to control the movement speed of the fluid.

Next, the light emitter 200 may emit light into the flow channel. The light emitter 200 may be disposed on one side of the flow channel, and include a laser diode for emitting laser light. Herein, the light emitted into the flow channel may be scattered through interaction with dust particles in the flow channel.

In a case, the light emitter 200 may include a diffusion lens for diffusing light. Herein, providing the light emitter 200 is intended to diffuse light such that the plurality of light detectors having different light detection ranges may accurately detect light.

In another case, the light emitter 200 may include a light absorber. The light absorber may be disposed to face the light emitter 200, and absorb light emitted from the light emitter 200. Herein, the reason for disposing the light absorber is that reflected light may be produced in the apparatus by reflection of light emitted from the light emitter 200, and function as noise in the light detector, thereby lowering reliability of a detection signal of the light detector.

Next, the light detector 300 may detect light scattered from the dust in the flow channel, and convert the same into an electrical detection signal. Herein, the light detector 300 may be configured by one detector having one light detection range.

For example, the light detector 300 may include a phototransistor for detecting light scattered from the dust in the flow channel and converting the same into an electrical signal.

As another example, the light detector 300 may include the phototransistor for detecting light scattered from the dust in the flow channel and converting the same into an electrical signal and an amplifier for amplifying the converted electrical signal from the phototransistor. Herein, the amplifier may include a transistor having a base connected to the emitter of the phototransistor, a collector connected to the collector of the phototransistor, and an emitter connected to the controller 400. In one embodiment, the amplifier may include a first transistor having a first base and first collector which are connected to the emitter of the phototransistor and a first emitter connected to the controller 400, a second transistor having a second base connected to the first base of the first transistor, a second collector connected to the collector of the phototransistor, and a second emitter connected to the controller, and a third transistor having a third base connected to the second base of the second transistor, a third collector connected to the collector of the phototransistor, and a third emitter connected to the controller 400.

In one embodiment, the light detector 300 may be configured by a plurality of detectors having different light detection ranges. The plurality of detectors may include a first detector for detecting light scattered within a first detection range in the light emission region of the flow channel and a second detector for detecting light scattered within a second detection range in the light emission region of the flow channel, the second detection range being narrower than the first detection range. The first detector may include a first lens having a first angle of view, and the second detector may include a second lens having a second angle of view, which is narrower than the first angle of view. In addition, the first detector may be disposed at a first distance from the central axis of the light emitted from the light emitter 200, and the second detector may be disposed at a second distance from the central axis of the light emitted from the light emitter 200. The first distance may be equal to the second distance. In addition, the first detector and the second detector may be disposed such that the central axis of the first detector and the central axis of the second detector intersect each other in the light emission region of the flow channel. Herein, the point at which the central axis of the first detector and the central axis of the second detector intersect each other may be a point which the central axis of the light emitted from the light emitter 200 crosses in the light emission region of the flow channel.

The light detector 300 may include a light absorber disposed to face the same. Herein, the light absorber may be disposed to face the corresponding light detector 300 with respect to the central axis of the light emitted from the light emitter 200, and may absorb light scattered from the dust in the flow channel. The reason for disposing the light absorber is that scattering light scattered from the dust may function as noise against the light detectors, thereby lowering reliability of detection signals of the light detectors.

The controller 400 may control the flow channel defining unit 100, the light emitter 200, and the light detector 300. The controller 400 may check if a detection value received from the light detector 300 is within an effective measurement range. If the detection value is outside the effective measurement range, the controller 400 may vary the effective measurement range. If the detection value is within the varied effective measurement range, the controller 400 may measure the dust concentration based on the detection value. In varying the effective measurement range, the controller 400 may vary the impedance of a signal received from the light detector 300.

That is, in varying the effective measurement range, the controller 400 may increase the maximum and minimum values in the effective measurement range if the detection value is greater than or equal to the maximum value in the effective measurement range, and may decrease the maximum and minimum values in the effective measurement range if the detection value is less than or equal to the minimum value in the effective measurement range. The controller 400 may decrease the impedance of the signal received from the light detector 300 to increase the maximum and minimum values in the effective measurement range, and may increase the impedance of the signal received from the light detector 300 to decrease the maximum and minimum values in the effective measurement range.

In one embodiment, the controller 400 may vary the effective measurement range according to preset variation levels. The preset variation levels may include a high-concentration level for varying the effective measurement range to a high-concentration measurement range and a low-concentration level for varying the effective measurement range to a low-concentration measurement range. For example, the maximum value in the high-concentration measurement range may be greater than the maximum and minimum values in the effective measurement range, and the minimum value in the high-concentration measurement range may be less than the maximum value in the effective measurement range and greater than the minimum value in the effective measurement range. In addition, the maximum value in the low-concentration measurement range may be less than the maximum value in the effective measurement range and greater than the minimum value in the effective measurement range, and the minimum value in the low-concentration measurement range may be less than the maximum and minimum values in the effective measurement range. Herein, the high-concentration measurement range and the low-concentration measurement range may partially overlap the effective measurement range.

In one embodiment, the preset variation levels may include a high-concentration level for varying the effective measurement range to one of multiple high-concentration measurement ranges and a low-concentration level for varying the effective measurement range to one of multiple low-concentration measurement ranges. Herein, the maximum value in a high-concentration measurement range adjacent to the effective measurement range may be greater than the maximum and minimum values in the effective management range, and the minimum value in the high-concentration measurement range adjacent to the effective measurement range may be less than the maximum value in the effective measure range and greater than the minimum value in the effective measurement range. In addition, the maximum value in a low-concentration measurement range adjacent to the effective measurement range may be less than the maximum value in the effective measurement range and greater than the minimum value in the effective measurement range, and the minimum value in the low-concentration measurement range adjacent to the effective measure range may be less than the maximum and minimum values in the effective measurement range. Herein, the high-concentration measurement range and low-concentration measurement range adjacent to the effective measure range may partially overlap the effective measure range.

Further, the controller 400 may include a measurement range adjuster 410. The measurement range adjuster 410 may vary the effective measure range according to the detection value received from the light detector 300.

For example, the measurement range adjuster 410 may include a plurality of diodes connected in series such that the input terminals of the diodes are connected to the output terminal of the light detector 300, and the output terminals of the diodes are grounded.

The measurement range adjuster 410 may further include an effective measurement range calculator and an effective measurement range variation unit. The effective measurement range calculator may calculate an effective measurement range by processing a signal received from the light detector 300. The effective measurement range variation unit may vary the effective measurement range if the detection value received from the light detector is outside the calculated effective measurement range.

For example, the effective measurement range calculator may include an analog front end (AFE) unit having an input terminal connected to the output terminal of the light detector, and the effective measurement range variation unit may include a DC offset cancellation unit having an input terminal connected to the output of the light detector and the output terminal of the AFE unit and a grounded output terminal.

As another example, the effective measurement range calculator may include an amplifier having an input terminal connected to the output terminal of the light detector, a first resistor connected to the output terminal of the amplifier, a capacitor having an input terminal connected to the first resistor and a grounded output terminal, and a second resistor having an input terminal connected to a node between the first resistor and the capacitor and a grounded output terminal. The effective measurement range variation unit may include a transistor having a base connected to the node between the first resistor and the capacitor and a collector connected to the output terminal of the light detector 300, and a third resistor having an input terminal connected to the emitter of the transistor and a grounded output terminal.

As another example, the effective measurement range calculator may include an amplifier having an input terminal connected to the output terminal of the light detector 300, a first resistor connected to the output terminal of the amplifier, a capacitor having an input terminal connected to the first resistor and a grounded output terminal, and a second resistor having an input terminal connected to a node between the first resistor and the capacitor and a grounded output terminal. The effective measurement range variation unit may include a first transistor having a first base subjected to a bias voltage and a first collector connected to the output terminal of the light detector 300, a second transistor having a second base connected to the node between the first resistor and the capacitor and a second collector connected to the first emitter of the first transistor, and a third resistor having an input terminal connected to the second emitter of the second resistor and a grounded output terminal.

As another example, the effective measurement range calculator may include an amplifier having an input terminal connected to the output terminal of the light detector 300, an AFE unit connected to the output terminal of the amplifier, an analog-to-digital converter (ADC) connected to the output terminal of the AFE unit, a digital-to-analog converter (DAC) connected to the output terminal of the ADC unit, a first resistor connected to the output terminal of the DAC unit, and a capacitor having an input terminal connected to the output terminal of the first resistor and a grounded output terminal. And the effective measurement range variation unit may include a first transistor having a first base subjected to a bias voltage and a first collector connected to the output terminal of the light detector 300, a second transistor having a second base connected to the node between the first register and the capacitor and a second collector connected to the first emitter of the first transistor, and a second resistor having an input terminal connected to the second emitter of the second transistor and a grounded output terminal.

As another example, the effective measurement range calculator may include an amplifier having an input terminal connected to the output terminal of the light detector 300, an AFE unit connected to the output terminal of the amplifier, a pulse width modulation (PWM) unit connected to the output terminal of the AFE unit, and a low pass filter (LPF) connected to the output terminal of the PWM unit. The effective measurement range variation unit may include a first transistor having a first base subjected to a bias voltage and a first collector connected to the output terminal of the light detector 300, a second transistor having a second base connected to the output terminal of the LPF and a second collector connected to the first emitter of the first transistor, and a second resistor having an input terminal connected to the second emitter of the second transistor and a grounded output terminal.

The controller 400 may widen or narrow the effective measurement range according to the amplification rate of a signal received from the light detector 300. For example, when the amplification rate of the signal received from the light detector 300 increases, the controller 400 may increase the maximum value in the effective measurement range and decrease the minimum value in the effective measurement range, thereby widening the effective measurement range. When the amplification rate of the signal received from the light detector 300 decreases, the controller 400 may decrease the maximum value in the effective measurement range and increase the minimum value in the effective measurement range, thereby narrowing the effective measurement range.

For example, provided that the light detector 300 includes a first detector for detecting light scattered within a first detection range in the light emission region of a flow channel and a second detector for detecting light scattered within a second detection range narrower than the first detection range in the light emission region of the flow channel, when the controller 400 receives a first detection value from the first detector, the controller 400 may check if the first detection value is within a first effective measurement range. When the controller 400 receives a second detection value from the second detector, the controller 400 may check if the second detection value is within a second effective measurement range. Herein, the maximum value in the second effective measurement range may be greater than the maximum value in the first effective measurement range, and the minimum value in the second effective measurement range may be greater than the minimum value in the first effective measurement range.

The dust measuring apparatus 1000 may further include a communication unit for establishing communication with an external terminal. When communication with the external terminal is established, the controller 400 may transmit measured dust concentration information to the external terminal. When the controller 400 receives a control signal from the external terminal, the controller 400 may vary the effective measurement range according to the receiver control signal, measure a dust concentration based on the varied effective measurement range, and transmit the measured dust concentration information to the external terminal. When the controller transmits the dust concentration information, the controller may provide the external terminal with guide information for guiding adjustment of the effective measurement range.

In one embodiment, the dust measuring apparatus 1000 may further include a sensing unit for sensing a current position thereof. When communication with the external terminal is established, the controller 400 may transmit, to the external terminal, the current position information and the dust concentration information measured at the current position.

As described above, according to an embodiment of the present invention, the measurement range of dust concentrations may be widened by varying the effective measurement range within which dust measurement is possible.

In addition, according to an embodiment of the present invention, in varying the effective measurement range, the impedance of a signal received from the light detector is varied. Thereby, circuit configuration may be simplified.

In addition, according to an embodiment of the present invention, measurement precision may be enhanced by varying the effective measurement range according to a plurality of preset variation levels.

In addition, according to an embodiment of the present invention, a high-concentration measurement range and a low-concentration measurement range which are adjacent to the effective measurement range are configured to partially overlap the effective measurement range. Thereby, reliability of dust concentration measurement may be enhanced.

In addition, according to an embodiment of the present invention, the effective measurement range may be widened or narrowed according to an amplification rate of a signal received from the light detector. Thereby, the measurement range of dust concentrations may be widened.

In addition, according to an embodiment of the present invention, the effective measurement range is readjusted according to the detection range performance of the light detector. Thereby, measurement precision may be enhanced.

In addition, according to an embodiment of the present invention, user convenience may be provided by transmitting, to an external terminal, dust concentration information measured at a current position and guide information for guiding adjustment of the effective measurement range.

In addition, according to an embodiment of the present invention, the effective measurement range may be manually varied by providing a setting window for setting the effective measurement range of a dust measuring apparatus. Thereby, the user may easily and simply control the dust measuring apparatus.

Further, according to an embodiment of the present invention, guide information for guiding ventilation is provided by collecting environment information about a current position of the dust measuring apparatus. Thereby, user convenience may be improved.

Figure 2:
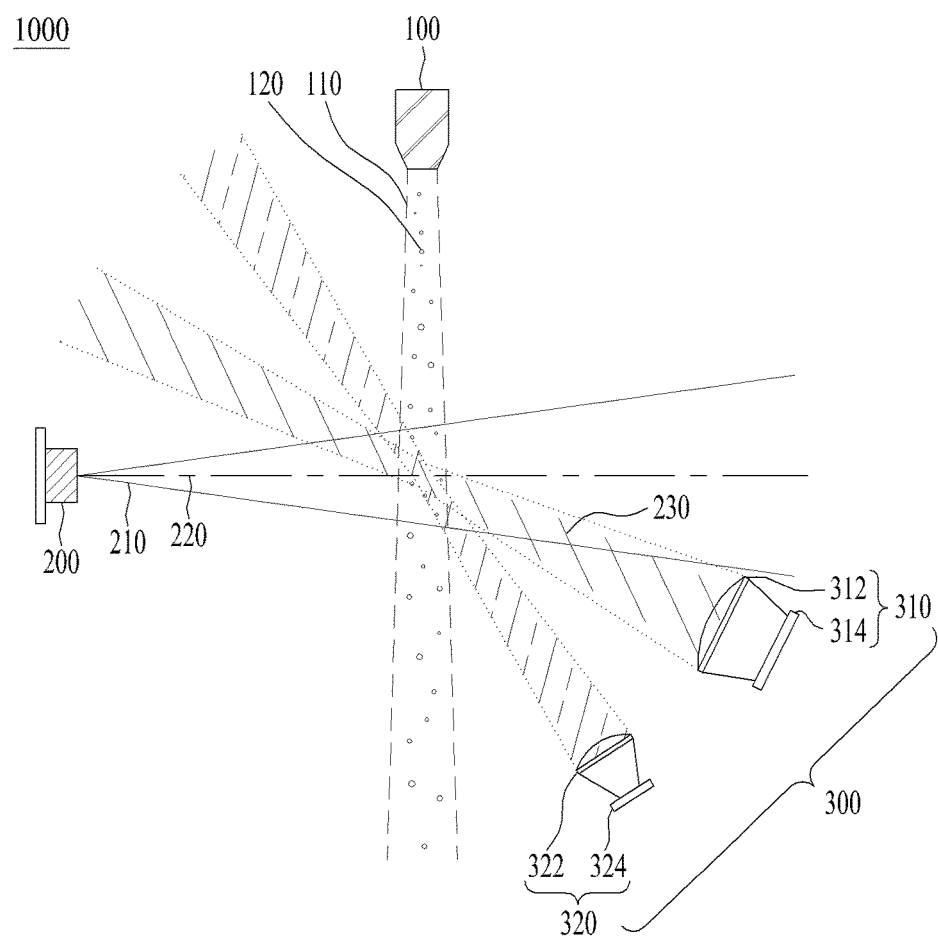
FIG. 2 illustrates arrangement of the light detector of FIG. 1.

FIG. 2 illustrates arrangement of the light detector of FIG. 1.

As shown in FIG. 2, the dust measuring apparatus 1000 may include a flow channel defining unit 100, a light emitter 200, and a light detector 300.

The flow channel defining unit 100 may define a flow channel 110 through which a fluid containing dust particles 120 moves.

The light emitter 200 may emit light 210 into the flow channel 110. Herein, the light 210 emitted into the flow channel 110 may be scattered through interaction with the dust particles 120 in the flow channel 110.

The light detector 300 may detect light 230 scattered from the dust particles 120 in the flow channel 110 and convert the same into an electrical detection signal. Herein, the light detector 300 may be configured by one detector having one light detection range.

For example, the light detector 300 may include a phototransistor for detecting the light 230 scattered from the dust particles 120 in the flow channel 110 and converting the same into an electrical signal.

As another example, the light detector 300 may include a phototransistor for detecting the light 230 scattered from the dust particles 120 in the flow channel 110 and converting the same into an electrical signal and an amplifier for amplifying the converted electrical signal from the phototransistor. Herein, the amplifier may include a transistor having a base connected to the emitter of the phototransistor, a collector connected to the collector of the phototransistor, and an emitter connected to the controller 400. In one embodiment, the amplifier may include a first transistor having a first base and a first collector which are connected to the emitter of the phototransistor and a first emitter connected to the controller 400, a second transistor having a second base connected to the first base of the first transistor, a second collector connected to the collector of the phototransistor, and a second emitter connected to the controller, and a third transistor having a third base connected to the second base of the second transistor, a third collector connected to the collector of the phototransistor, and a third emitter connected to the controller 400.

In one embodiment, the light detector 300 may be configured by a plurality of detectors having different light detection ranges. For example, the light detector 300 may include a plurality of detectors such as a first detector 310 and a second detector 320.

The first detector 310 may detect the light 230 scattered within a first detection range in the light emission region of the flow channel 110, and the second detector 320 may detect the light 230 scattered within a second detection range in the light emission region of the flow channel 110. The first detection range of the first detector 310 is wider than the second detection range of the second detector 320.

In addition, the first detector 310 may include a first lens 312 having a first angle of view and a first sensor 314, and the second detector 320 may include a second lens 322 having a second angle of view and a second sensor 324. The first angle of view of the first lens 312 of the first detector 310 is wider than the second angle of view of the second lens 322 of the second detector 320.

In addition, the first detector 310 and the second detector 320 may be disposed such that the central axes thereof intersect each other in the light emission region of the flow channel 110. Herein, the point at which the central axes of the first detector 310 and the second detector 320 intersect each other may be a point at which the central axis 220 of the light 210 emitted from the light emitter 200 crosses in the light emission region of the flow channel 110.

A measurement range adjuster of the controller may check if a detection value received from the light detector 300 is within an effective measurement range. If the detection value is outside the effective measurement range, the measurement range adjuster may vary the effective measurement range. If the detection value is within the varied effective measurement range, the measurement range adjuster may measure the dust concentration based on the detection value. In varying the effective measurement range, the measurement range adjuster of the controller may vary the impedance of a signal received from the light detector 300.

That is, in varying the effective measurement range, the measurement range adjuster of the controller may increase the maximum and minimum values in the effective measurement range if the detection value is greater than or equal to the maximum value in the effective measurement range, and may decrease the maximum and minimum values in the effective measurement range if the detection value is less than or equal to the minimum value in the effective measurement range. The measurement range adjuster of the controller may decrease the impedance of the signal received from the light detector 300 to increase the maximum and minimum values in the effective measurement range, and may increase the impedance of the signal received from the light detector 300 to decrease the maximum and minimum values in the effective measurement range. The impedance is varied for the following reason. When the impedance increases, the amplification rate of the signal increases, and thus even a very weak signal may be detected. When the impedance decreases, the amplification rate of the signal decreases, and thus even a very strong signal may be detected. Accordingly, the dust measuring apparatus according to this embodiment may increase the lower limit and upper limit of detectable concentrations of dust particles.

By varying the effective measurement range within which dust measurement is possible as above, the measurement range of dust concentrations may be widened.

Figure 3:
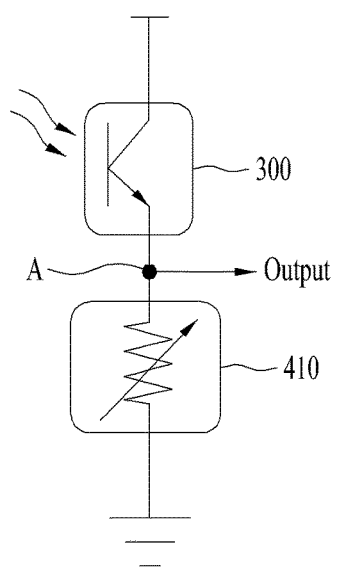
FIG. 3 is a circuit diagram illustrating the concept of the present invention.

FIG. 3 is a circuit diagram illustrating the concept of the present invention.

As shown in FIG. 3, the apparatus according to an embodiment of the present invention may include the light detector 300 and a measurement range adjuster 410. Herein, the light detector 300 may include a phototransistor for detecting light scattered from the dust in the flow channel and converting the same into an electrical signal. The measurement range adjuster 410 may vary the effective measurement range according to a detection value received from the light detector 300. In varying the effective measurement range, the measurement range adjuster 410 may vary the impedance of a signal received from the light detector 300. The measurement range adjuster 410 may be configured by various circuits capable of varying the impedance of a signal.

Figure 4:
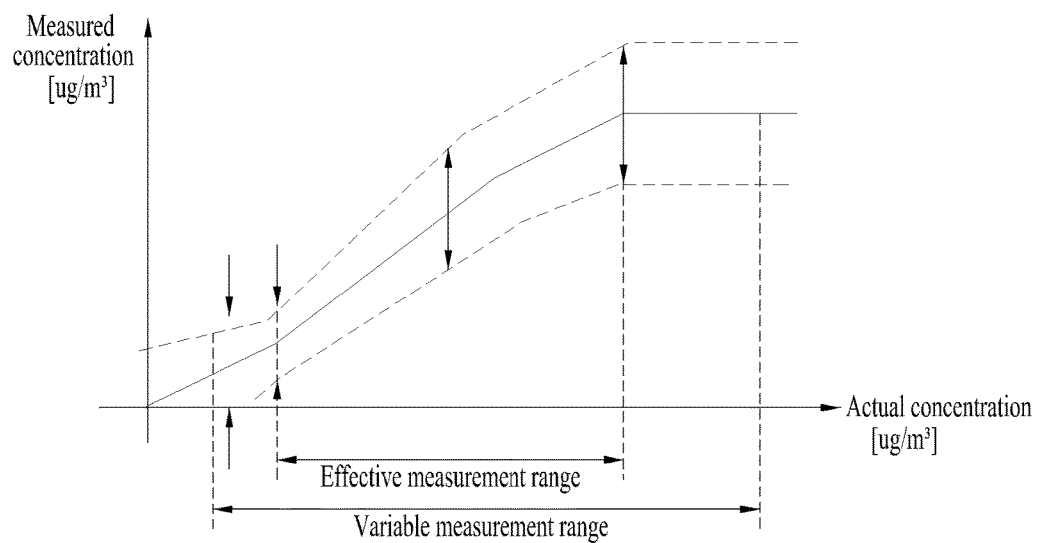
FIG. 4 is a graph depicting an effective measurement range of dust concentrations.

FIG. 4 is a graph depicting an effective measurement range of dust concentrations.

As shown in FIG. 4, the conventional light detector has a limited effective measurement range due to the circuit thereof, and thus may perform dust measurement within the effective measurement range. However, if the dust concentration is above or below the effective measurement range, it may be difficult to perform dust measurement. This is because an output signal of the light detector may be output normally for a dust concentration within the effective measurement range, but the output signal may be output abnormally for a dust concentration above or below the effective measurement range, due to limitation on the circuit of the light detector.

According to this embodiment, if the output signal of the light detector is output abnormally when the dust concentration is above or below the effective measurement range, signal processing is performed by varying the impedance for the output signal such that the output signal is placed within the effective measurement range. Thereby, high-concentration dust or low-concentration dust may be measured. That is, the effective measurement range of dust concentrations may be widened to a variable measurement range within which low-concentration dust in the high-concentration dust may be measured.

Figure 5:
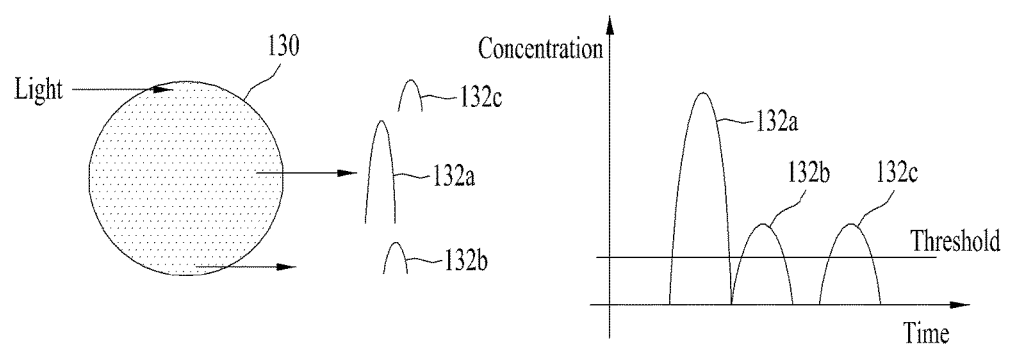
FIG. 5 illustrates output signals in an effective measurement range of typical concentrations.
Figure 6:
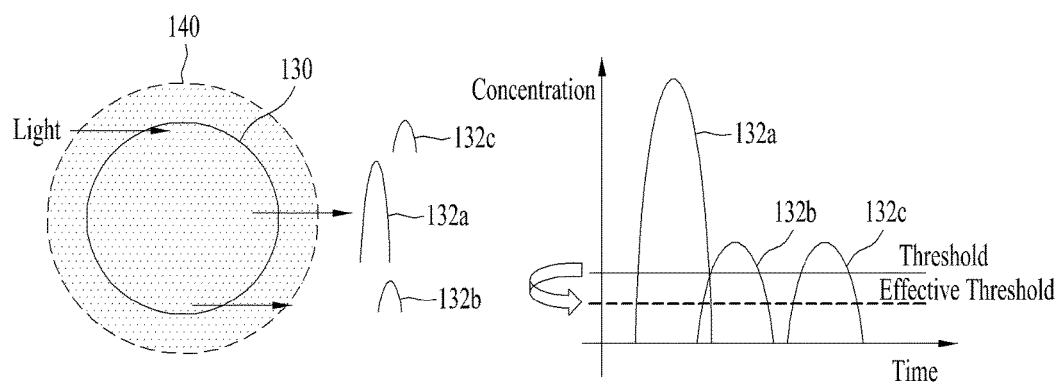
FIG. 6 illustrates output signals in an effective measurement range of low concentrations.
Figure 7:
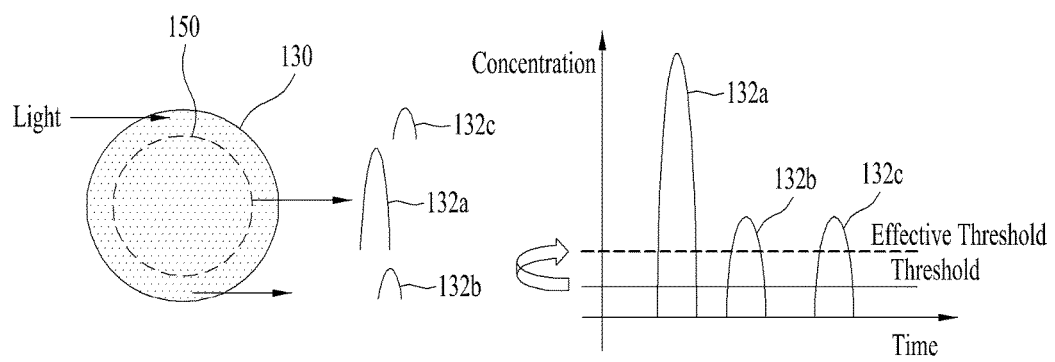
FIG. 7 illustrates output signals in an effective measurement range of high concentrations.

FIG. 5 illustrates output signals in an effective measurement range of typical concentrations, FIG. 6 illustrates output signals in an effective measurement range of low concentrations, and FIG. 7 illustrates output signals in an effective measurement range of high concentrations.

As shown in FIG. 5, when light is received from the measurement region 130 having dust of a typical concentration, a first output signal 132a received from the middle region of the measurement region 130 may have the highest strength, and second and third output signals 132b and 132c received from first and second edge regions may have the lowest strength. Herein, for the first, second and third output signals 132a, 132b and 132c, since the average value of dust concentrations corresponds to a reference value, dust concentrations may be measured without varying the impedance.

As shown in FIG. 6, when light is received from the measurement region 130 having dust of a low concentration, the first output signal 132a received from the middle region of the measurement region 130 may have the highest strength, and the second and third output signals 132b and 132c received from the first and second edge regions of the measurement region 130 may have the lowest strength. Herein, for the first, second and third output signals 132a, 132b and 132c, since the average value of dust concentrations is less than the reference value, it is difficult to measure the dust concentration. Accordingly, in this embodiment, if the impedance of the output signal is increased to increase the amplification rate of the output signal, the measurement region 130 may be widened even to a low-concentration measurement region 140. Thereby, the low-concentration dust may be measured.

As shown in FIG. 7, when light is received from the measurement region 130 having high-concentration dust, the first output signal 132a received from the middle region of the measurement region 130 may have the highest strength, and the second and third output signals 132b and 132c received from the first and second edge regions of the measurement region 130 may have the lowest strength. Herein, for the first, second and third output signals 132a, 132b and 132c, since the average value of dust concentrations is greater than the reference value, it is difficult to measure the dust concentration. Accordingly, in this embodiment, if the impedance of the output signal is reduced to reduce the amplification rate of the output signal, the measurement region 130 may be widened even to a high-concentration measurement region 150. Thereby, high-concentration dust may be measured.

As described above, by varying the effective measurement range within which dust measurement is possible, the measurement range of dust concentrations may be widened.

FIGS. 8 to 11 illustrate a procedure of varying an effective measurement range according to dust concentrations.

Figure 8:
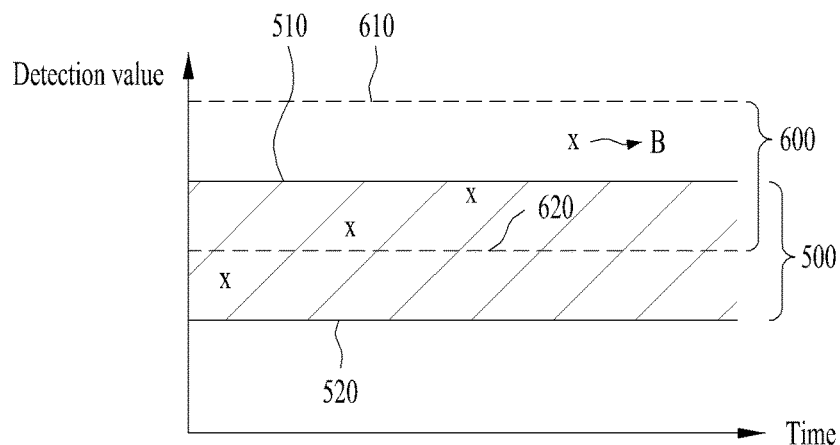
FIGS. 8 to 11 illustrate a procedure of varying an effective measurement range according to dust concentrations.

As shown in FIG. 8, the controller of the present invention may check if a detection value B received from the light detector is within an effective measurement range 500. Herein, the effective measurement range 500 may include a maximum value 510 and a minimum value 520. If the detection value is within the effective detection range, the dust concentration may be detected.

Subsequently, if the detection value B is greater than or equal to the maximum value 510 in the effective detection range 500, the controller may vary the effective detection range 500 to a high-concentration measurement range 600 within which high-concentration dust may be measured, and measure the high-concentration dust. Herein, the controller may reduce the impedance for the detection signal. Thereby, the controller may increase the maximum value 510 in the effective measurement range 500 to a maximum value 610 of the high-concentration measurement range 600, and increase the minimum value 520 in the effective measurement range 500 to a minimum value 620 in the high-concentration measurement range 600.

Figure 9:
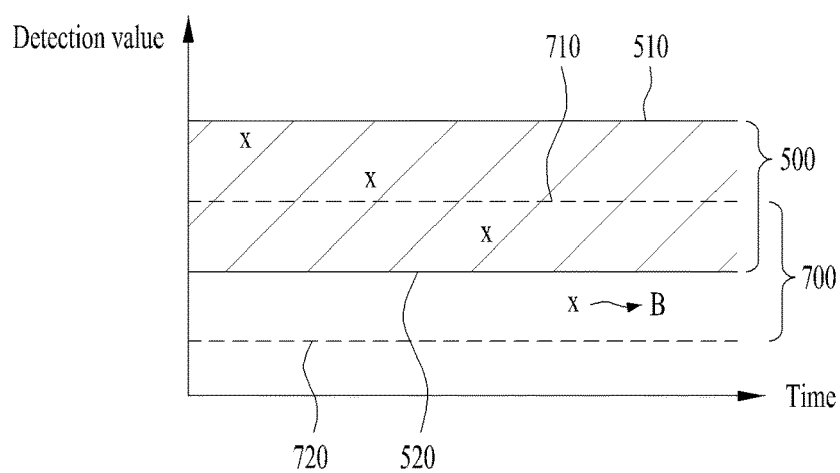
Figure 10:
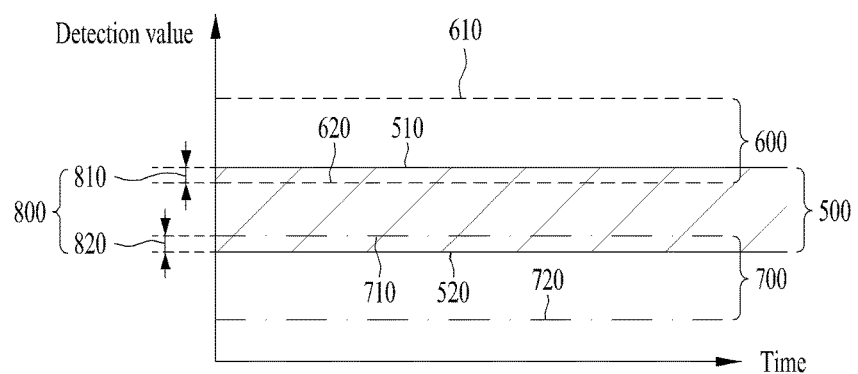

In addition, as shown in FIG. 9, the controller of the present invention may check if the receiver detection value B is within the effective measurement range 500. Herein, the effective measurement range 500 may include the maximum value 510 and the minimum value 520. If the detection value B is within the effective detection range, the controller may detect a dust concentration.

If the detection value B is less than or equal to the minimum value 520 in the effective measurement range 500, the controller may vary the effective detection range 500 to a low-concentration measurement range 700 within which measurement of low-concentration dust is possible, and measure the low-concentration dust. Herein, the controller may increase the impedance for the detection signal. Thereby, the controller may decrease the maximum value 510 and a maximum value 710 in the low-concentration measurement range 700, and decrease the minimum value 520 in the effective measurement range 500 to a minimum value 720 in the low-concentration measurement range 700.

As described above, the controller may vary the effective measurement range 500 if the detection value B is outside the effective measurement range 500, and may measure a dust concentration based on the detection value B if the detection value B is within the varied effective measurement range 500.

Next, in varying the effective measurement range 500, the controller may vary the effective measurement range 500 according to preset variation levels.

For example, the preset variation levels may include a high-concentration level for varying the effective measurement range 500 to the high-concentration measurement range 600 and a low-concentration level for varying the effective measurement range 500 to the low-concentration measurement range 700. Herein, the maximum value 610 in the high-concentration measurement range 600 may be greater than the maximum value 510 and minimum value 520 in the effective measurement range 500, and the minimum value 620 in the high-concentration measurement range 600 may be less than the maximum value 510 in the effective measurement range 500 and greater than the minimum value 520 in the effective measurement range 500. In addition, the maximum value 710 in the low-concentration measurement range 700 may be less than the maximum value 510 in the effective measurement range 500 and greater than the minimum value 520 in the effective measurement range 500, and the minimum value 720 in the low-concentration measurement range 700 may be less than the maximum value 510 and minimum value 520 in the effective measurement range 500.

In this way, the high-concentration measurement range 600 and the low-concentration measurement range 700 may have an overlapping region 800 that overlaps the effective measurement range 500. Herein, the high-concentration measurement range 600 and the effective measurement range 500 may share a first overlapping region 810, and the low-concentration measurement range 700 and the effective measurement range 500 may share a second overlapping region 820. This is because it may be difficult to measure a detection value in a boundary region between the high-concentration measurement range 600 and the low-concentration measurement range 700 if the overlapping region 800 does not exist between the high-concentration measurement range 600 and the low-concentration measurement range 700.

Figure 11:
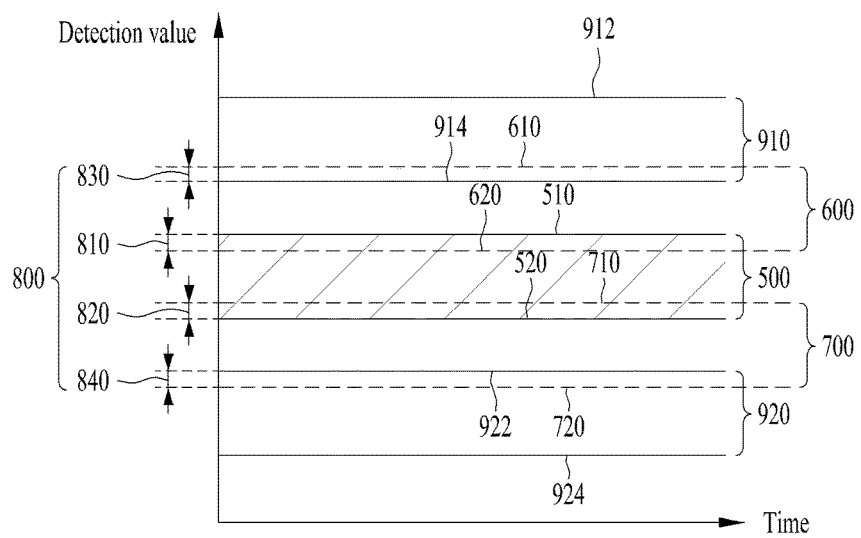

As another example, as shown in FIG. 11, the preset various levels may include a high-concentration level for varying the effective measurement range 500 to one high-concentration measurement range 600 between multiple high-concentration measurement ranges 600 and 910 and a low-concentration level for varying the effective measurement range 500 to one low-concentration measurement range 700 between multiple low-concentration measurement ranges 920 and 700. Herein, the maximum value 610 in the high-concentration measurement range 600 adjacent to the effective measurement range 500 may be greater than the maximum value 510 and minimum value 520 in the effective management range 500, and the minimum value 620 in the high-concentration measurement range 600 adjacent to the effective measurement range 500 may be less than the maximum value 510 in the effective measure range 500 and greater than the minimum value 520 in the effective measurement range 500. In addition, the maximum value 710 in the low-concentration measurement range 700 adjacent to the effective measurement range 500 may be less than the maximum value 510 in the effective measurement range 500 and greater than the minimum value 520 in the effective measurement range 500, and the minimum value 720 in the low-concentration measurement range 700 adjacent to the effective measure range 500 may be less than the maximum value 510 and minimum value 520 in the effective measurement range 500.

As described above, the high-concentration measurement range 600 and the low-concentration measurement range 700 which are adjacent to the effective measurement range 500 may partially overlap the effective measurement range 500 through the overlapping region 800 provided thereto. Herein, the high-concentration measurement range 600 and the effective measurement range 500 may share the first overlapping region 810, and the low-concentration measurement range 700 and the effective measurement range 500 may share the second overlapping region 820. This is because it may be difficult to measure a detection value in a boundary region between the high-concentration measurement range 600 and the low-concentration measurement range 700 if the overlapping region 800 does not exist between the high-concentration measurement range 600 and the low-concentration measurement range 700.

The high-concentration measurement ranges 600 and 910 adjacent to each other may also share an overlapping region 800, and the low-concentration measurement ranges 700 and 920 adjacent to each other may also share an overlapping region 800. Specifically, the high-concentration measurement ranges 600 and 910 may share a third overlapping region 830, and the low-concentration measurement ranges 700 and 920 may share a fourth overlapping region 840.

By varying the effective measurement range according to multiple preset variation labels as described above, measurement precision may be enhanced.

In addition, according to an embodiment of the present invention, the high-concentration measurement range and low-concentration measurement range adjacent to the effective measurement range are configured to partially overlap the effective measurement range. Thereby, reliability of dust concentration measurement may be enhanced.

FIGS. 12 to 17 are circuit diagrams illustrating the measurement range adjuster of FIG. 1.

As shown in FIGS. 12 to 17, the controller of the present invention may include a measurement range adjuster 410. The measurement range adjuster 410 may vary the effective measurement range according to a detection value received from the light detector 300.

Figure 12:
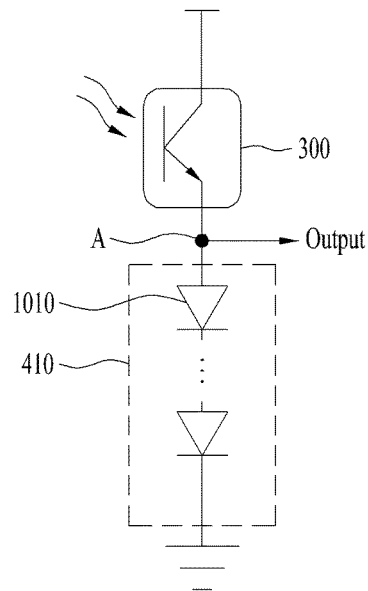
FIGS. 12 to 17 are circuit diagrams illustrating the measurement range adjuster of FIG. 1.

For example, as shown in FIG. 12, the measurement range adjuster 410 may include a plurality of diodes 1010 connected in series such that the input terminals of the diodes 1010 are connected to the output terminal of the light detector 300, and the output terminals of the diodes 1010 are grounded. Herein, when an average current value increases along with increase in the dust concentration, the measurement range adjuster 410 may decrease the impedance of the diodes 1010 such that high-concentration dust is measurable. When the average current value decreases along with decrease in the dust concentration, the measurement range adjuster 410 may increase the impedance of the diodes 1010 such that low-concentration dust is measurable.

Figure 13:
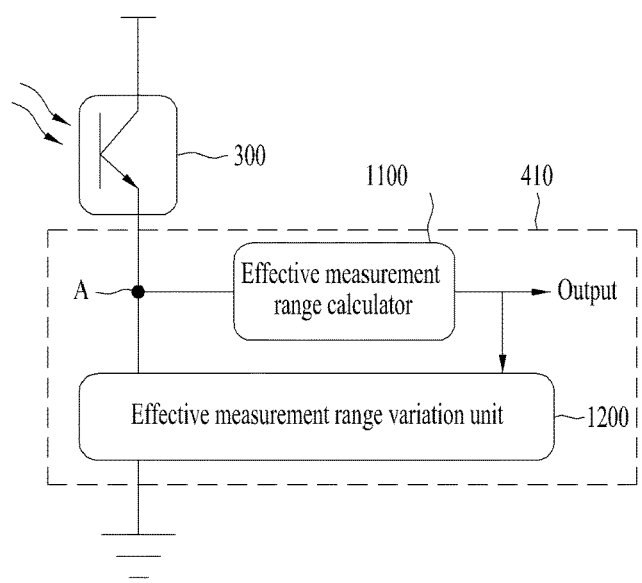

As an example, as shown in FIG. 13, the measurement range adjuster 410 may include an effective measurement range calculator 1100 and an effective measurement range variation unit 1200. The effective measurement range calculator 1100 may calculate an effective measurement range by processing a signal received from the light detector 300. The effective measurement range variation unit 1200 may vary the effective measurement range if the detection value received from the light detector 300 is outside the calculated effective measurement range. The effective measurement range calculator 1100 may include an analog front end (AFE) unit having an input terminal connected to the output terminal of the light detector 300, and the effective measurement range variation unit may include a DC offset cancellation unit having an input terminal connected to the output of the light detector 300 and the output terminal of the AFE unit and a grounded output terminal. The DC offset cancellation unit may vary a DC signal of node A.

Figure 14:
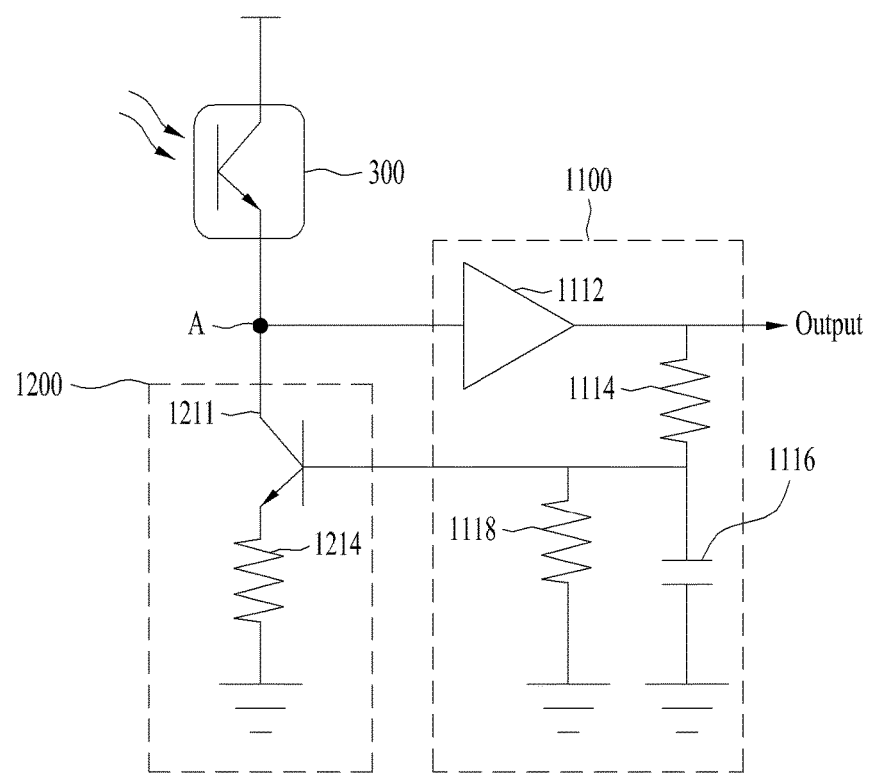
Figure 15:
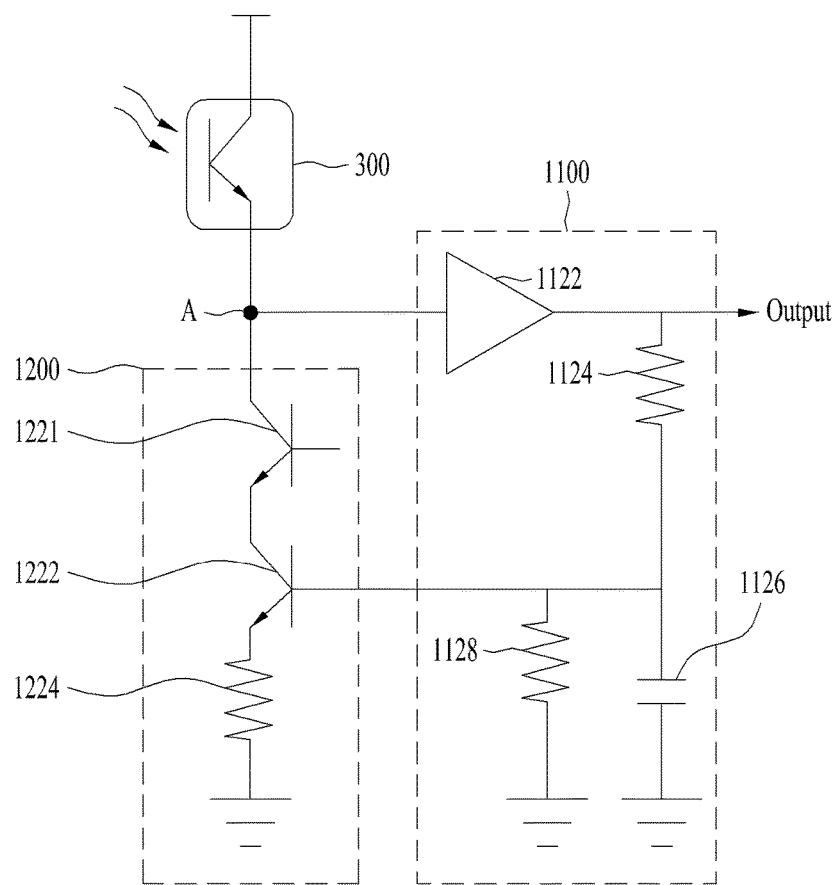

As another example, as shown in FIG. 14, the effective measurement range calculator 1100 may include an amplifier 1112 having an input terminal connected to the output terminal of the light detector, a first resistor 1114 connected to the output terminal of the amplifier 1112, a capacitor 1116 having an input terminal connected to the first resistor 1114 and a grounded output terminal, and a second resistor 1118 having an input terminal connected to a node between the first resistor 1114 and the capacitor 1116 and a grounded output terminal. The effective measurement range variation unit 1200 may include a transistor 1211 having a base connected to the node between the first resistor 1114 and the capacitor 1116 and a collector connected to the output terminal of the light detector 300, and a third resistor 1214 having an input terminal connected to the emitter of the transistor 1211 and a grounded output terminal. Herein, the effective measurement range variation unit 1200 may vary the impedance for an AC signal to vary the DC signal of node A.

As another example, the effective measurement range calculator 1100 may include an amplifier 1122 having an input terminal connected to the output terminal of the light detector 300, a first resistor 1124 connected to the output terminal of the amplifier 1122, a capacitor 1126 having an input terminal connected to the first resistor 1124 and a grounded output terminal, and a second resistor 1128 having an input terminal connected to a node between the first resistor 1124 and the capacitor 1126 and a grounded output terminal. The effective measurement range variation unit 1200 may include a first transistor 1221 having a first base subjected to a bias voltage and a first collector connected to the output terminal of the light detector 300, a second transistor 1222 having a second base connected to the node between the first resistor 1124 and the capacitor 1126 and a second collector connected to the first emitter of the first transistor 1221, and a third resistor 1224 having an input terminal connected to the second emitter 1222 of the second resistor and a grounded output terminal.

Figure 16:
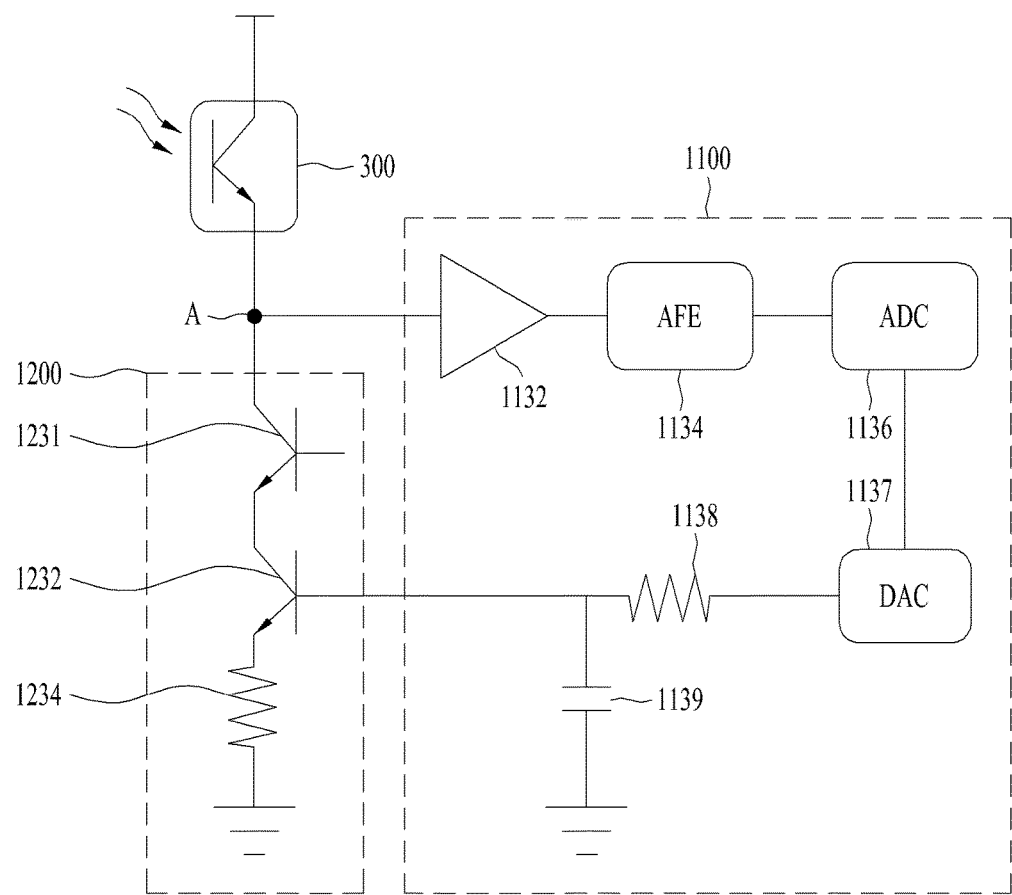

As another example, as shown in FIG. 16, the effective measurement range calculator 1100 may include an amplifier 1132 having an input terminal connected to the output terminal of the light detector 300, an AFE unit 1134 connected to the output terminal of the amplifier 1132, an analog-to-digital converter (ADC) 1136 connected to the output terminal of the AFE unit 1134, a digital-to-analog converter (DAC) 1137 connected to the output terminal of the ADC unit 1136, a first resistor 1138 connected to the output terminal of the DAC unit 1137, and a capacitor 1139 having an input terminal connected to the output terminal of the first resistor 1138 and a grounded output terminal. The effective measurement range variation unit 1200 may include a first transistor 1231 having a first base subjected to a bias voltage and a first collector connected to the output terminal of the light detector 300, a second transistor 1232 having a second base connected to the node between the first resistor 1138 and the capacitor 1139 and a second collector connected to the first emitter of the first transistor 1231, and a second resistor 1234 having an input terminal connected to the second emitter of the second transistor 1232 and a grounded output terminal.

Figure 17:
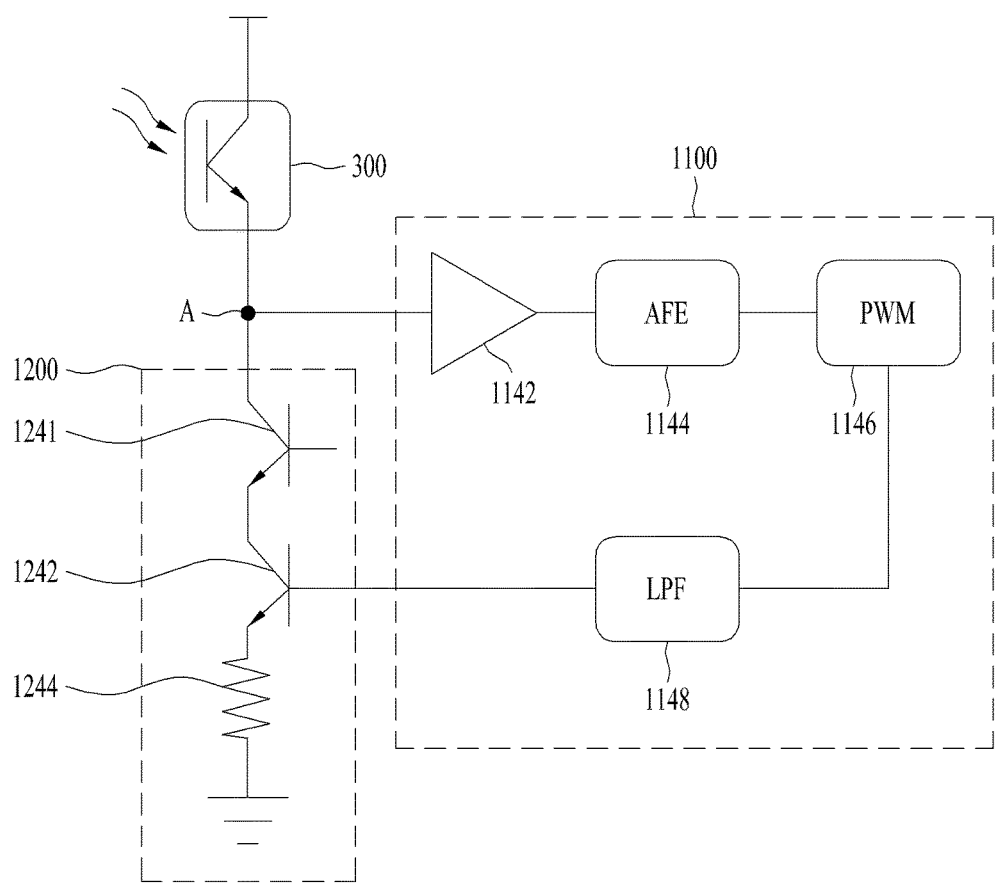

As another example, as shown in FIG. 17, the effective measurement range calculator 1100 may include an amplifier 1142 having an input terminal connected to the output terminal of the light detector 300, an AFE unit 1144 connected to the output terminal of the amplifier 1142, a pulse width modulation (PWM) unit 1146 connected to the output terminal of the AFE unit 1144, and a low pass filter (LPF) 1148 connected to the output terminal of the PWM unit 1146. The effective measurement range variation unit 1200 may include a first transistor 1241 having a first base subjected to a bias voltage and a first collector connected to the output terminal of the light detector 300, a second transistor 1242 having a second base connected to the output terminal of the LPF 1148 and a second collector connected to the first emitter of the first transistor 1241, and a second resistor 1244 having an input terminal connected to the second emitter of the second transistor 1242 and a grounded output terminal.

As described above, according to an embodiment of the present invention, a circuit for varying the impedance of a signal received from the light detector may be configured in various ways, and the circuit configuration may be simplified.

Accordingly, with the simple circuit configuration, the effective measurement range may be widened by varying the impedance of a signal such that any kind of dust from high-concentration dust to low-concentration dust may be measured.

Figure 18:
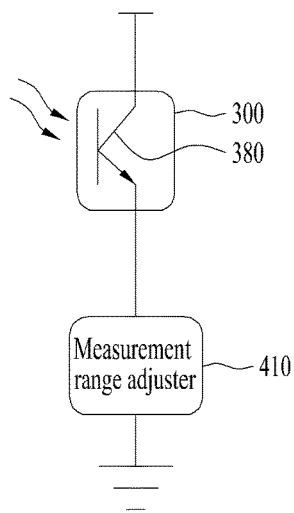
FIGS. 18 to 20 are circuit diagrams illustrating the light detector of FIG. 1.
Figure 19:
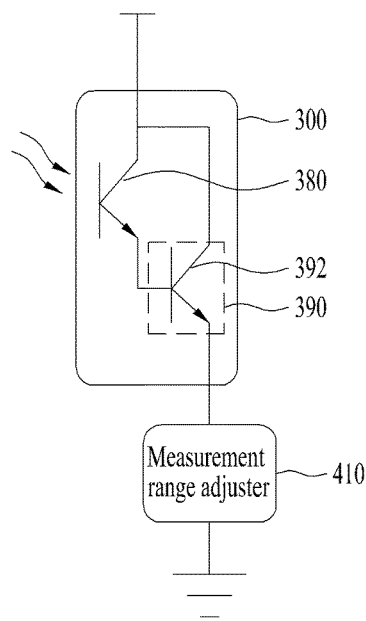
Figure 20:
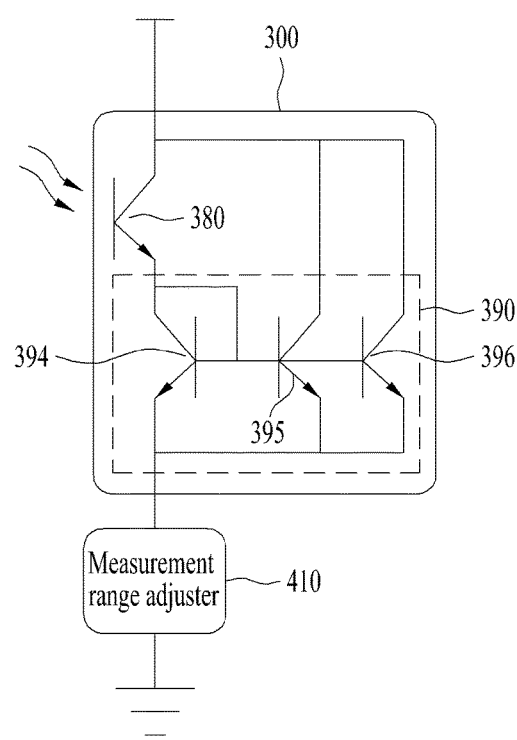

FIGS. 18 to 20 are circuit diagrams illustrating the light detector of FIG. 1.

As shown in FIGS. 12 to 20, the light detector 300 may detect light scattered from the dust in the flow channel, and convert the same into an electrical detection signal. Herein, the light detector 300 may be configured by one detector having one light detection range or by multiple detectors having multiple light detection ranges.

For example, as shown in FIG. 18, the light detector 300 may include a phototransistor 380 for detecting light scattered from the dust in the flow channel and converting the same into an electrical signal. The output terminal of the phototransistor 380 may be electrically connected to the measurement range adjuster 410 of the controller.

As another example, as shown in FIGS. 19 and 20, the light detector 300 may include the phototransistor 380 for detecting light scattered from the dust in the flow channel and converting the same into an electrical signal and an amplifier 390 for amplifying the converted electrical signal from the phototransistor.

As shown in FIG. 19, the amplifier 390 may include a transistor 392 having a base connected to the emitter of the phototransistor 380, a collector connected to the collector of the phototransistor 380, and an emitter connected to the measurement range adjuster 410.

In one embodiment, as shown in FIG. 20, the amplifier 390 may include a first transistor 394 having a first base and first collector which are connected to the emitter of the phototransistor 380 and a first emitter connected to the measurement range adjuster 410 of the controller, a second transistor 395 having a second base connected to the first base of the first transistor 394, a second collector connected to the collector of the phototransistor 380, and a second emitter connected to the measurement range adjuster 410 of the controller, and a third transistor 396 having a third base connected to the second base of the second transistor 395, a third collector connected to the collector of the phototransistor 380, and a third emitter connected to the measurement range adjuster 410 of the controller.

The reason for manufacturing the light detector 300 with the circuit configuration for amplifying an output signal is that an effective measurement range may be widened and narrowed according to the amplification rate of a signal received from the light detector 300. That is, according to an embodiment of the present invention, measurement precision may be enhanced by readjusting the effective measurement range according to the detection range performance of the light detector 300.

The measurement range adjuster 410 of the controller may widen or narrow the effective measurement range according to the amplification rate of the signal received from the light detector 300. For example, when the amplification rate of the signal received from the light detector 300 increases, the measurement range adjuster 410 of the controller may increase the maximum value in the effective measurement range and decrease the minimum value in the effective measurement range, thereby widening the effective measurement range. When the amplification rate of the signal received from the light detector 300 decreases, the measurement range adjuster 410 may decrease the maximum value in the effective measurement range and increase the minimum value in the effective measurement range, thereby narrowing the effective measurement range.

For example, provided that the light detector 300 includes a first detector for detecting light scattered within a first detection range in the light emission region of a flow channel and a second detector for detecting light scattered within a second detection range narrower than the first detection range in the light emission region of the flow channel, when the controller 400 receives a first detection value from the first detector, the controller 400 may check if the first detection value is within a first effective measurement range. When the controller 400 receives a second detection value from the second detector, the controller 400 may check if the second detection value is within a second effective measurement range. Herein, the maximum value in the second effective measurement range may be greater than the maximum value in the first effective measurement range, and the minimum value in the second effective measurement range may be greater than the minimum value in the first effective measurement range.

As described above, according to an embodiment of the present invention, the measurement range of dust concentrations may be widened by widening or narrowing the effective measurement range according to the amplification rate of a signal received from the light detector.

In addition, according to an embodiment of the present invention, measurement precision may be enhanced by readjusting the effective measurement range according to the detection range performance of the light detector.

Figure 21:
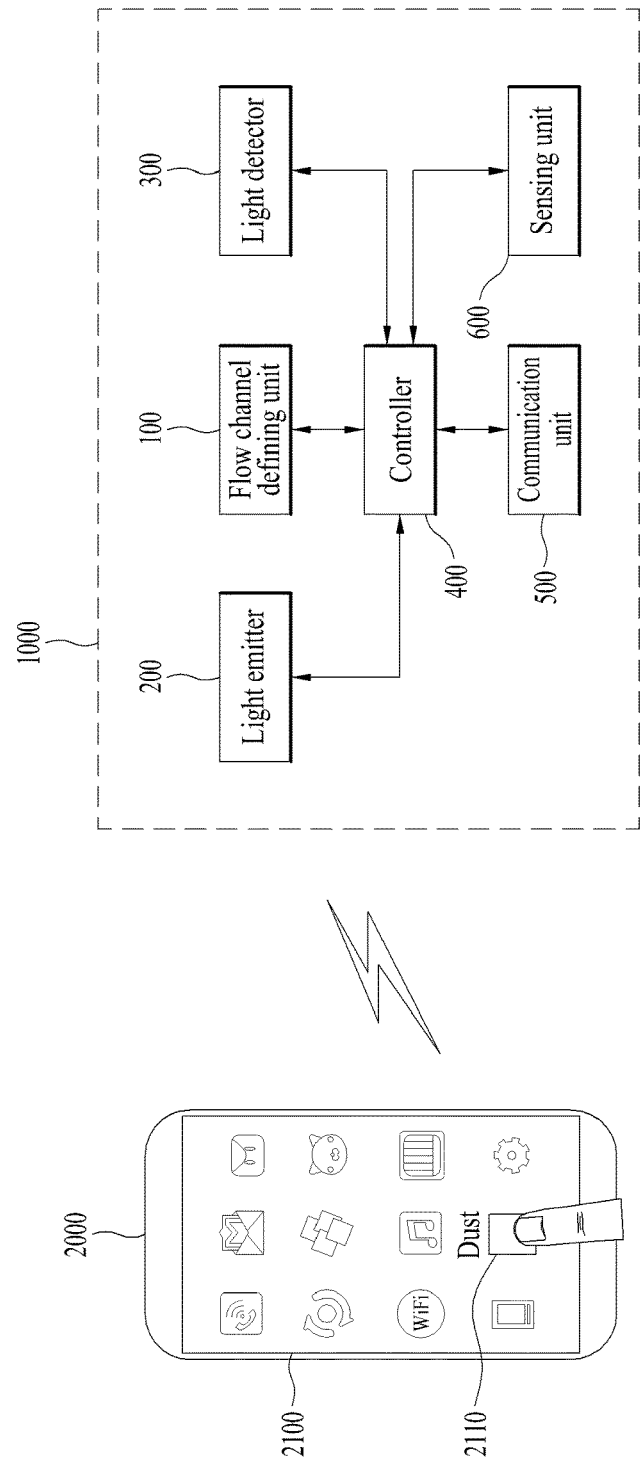
FIG. 21 illustrates establishment of communication between a dust measuring apparatus and a mobile terminal according to an embodiment of the present invention.

FIG. 21 illustrates establishment of communication between a dust measuring apparatus and a mobile terminal according to an embodiment of the present invention.

As shown in FIG. 21, the dust measuring apparatus 1000 may further include a communication unit 500 for establishing communication with a mobile terminal 2000. When communication with the mobile terminal 2000 is established, the controller 400 may transmit measured dust concentration information to the mobile terminal 2000. When the controller 400 receives a control signal from the mobile terminal 2000, the controller 400 may vary the effective measurement range according to the receiver control signal, measure a dust concentration based on the varied effective measurement range, and transmit the measured dust concentration information to the mobile terminal 2000. When the controller transmits the dust concentration information, the controller may provide the mobile terminal 2000 with guide information for guiding adjustment of the effective measurement range.

In one embodiment, the dust measuring apparatus 1000 may further include a sensing unit 600 for sensing a current position thereof. When communication with the mobile terminal 2000 is established, the controller 400 may transmit, to the mobile terminal 2000, the current position information and the dust concentration information measured at the current position.

When a dust measurement control icon 2110 displayed on a display screen 2100 is selected by user input, the mobile terminal 2000 may establish communication with the dust measuring apparatus 1000, recognizing that the user input is in the control mode of the dust measuring apparatus 1000.

Subsequently, once communication is established, the mobile terminal 2000 may display, on the display screen 2100, a setting window for setting an effective measurement range of the dust measuring apparatus 1000. Once the effective measurement range is set in the setting window, the mobile terminal 2000 may transmit, to the dust measuring apparatus 1000, a control signal corresponding to the set effective measurement range. Herein, the mobile terminal 2000 may establish communication with one dust measuring apparatus 1000 or multiple dust measuring apparatuses 1000.

As described above, according to an embodiment of the present invention, user convenience may be provided by transmitting, to a mobile terminal, dust concentration information measured at the current position and guide information for guiding adjustment of the effective measurement range.

Figure 22:
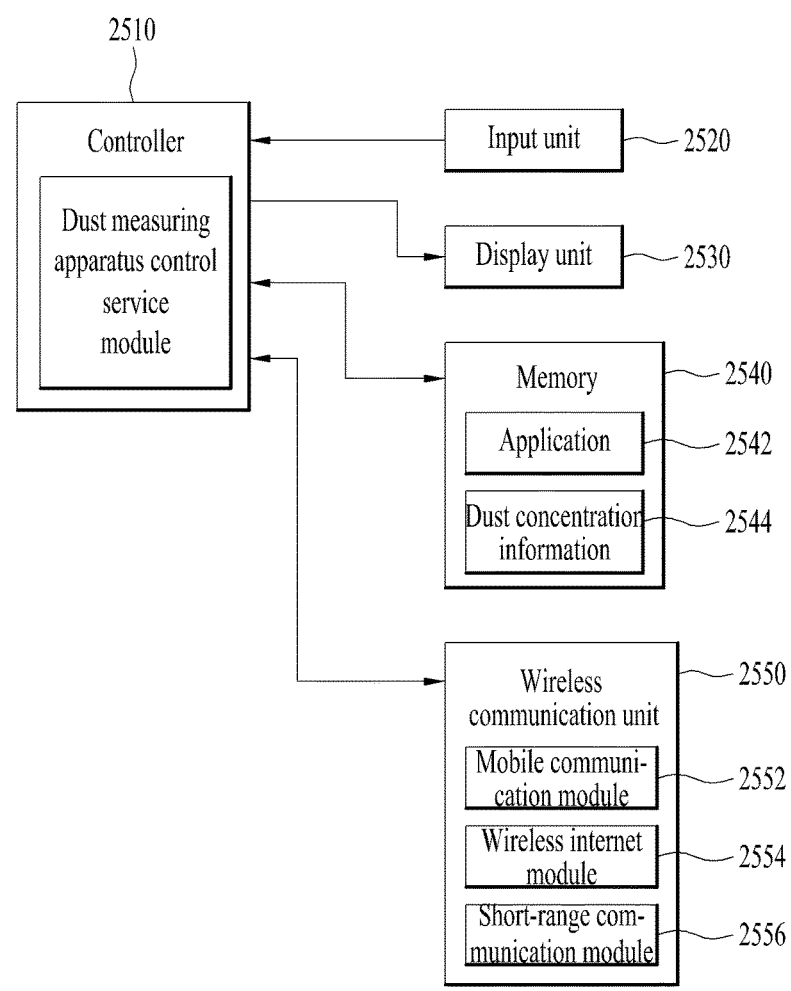
FIG. 22 is a block diagram illustrating a mobile terminal for controlling a dust measuring apparatus according to an embodiment of the present invention.

FIG. 22 is a block diagram illustrating a mobile terminal for controlling a dust measuring apparatus according to an embodiment of the present invention.

Referring to FIG. 20, the mobile terminal 2000 according to an embodiment includes a controller 2510, an input unit 2520, a display unit 2530, a memory 2540, and a wireless communication unit 2550.

Herein, the memory 2540 may store an application 2542. While FIG. 22 illustrates only one application 2542, a plurality of applications may be stored in the memory 2540. The application 2542 may be a native application which is installed when the mobile terminal 2000 is shipped or OS/firmware upgrade is performed, or may be an application which is a separately downloaded from the server and installed by the user.

Dust concentration information 2544 may also be stored in the memory 2540. In one embodiment, guide information for guiding adjustment of the effective measurement range and information about the current position of the dust measuring apparatus may be stored in the memory 2540.

The wireless communication unit 2550 may include a mobile communication module 2552, a Wireless Internet module 2554 and a short-range communication module 2556. The wireless communication unit 2550 may transmit a dust measurement control signal to the dust measuring apparatus, and receive dust concentration information from the dust measuring apparatus.

Next, the display unit 2530 may display a setting window for setting an effective measurement range of the dust measuring apparatus.

In addition, the input unit 2520 may receive user input.

The controller 2510 may include a control service module of the dust measuring apparatus. While FIG. 22 illustrates that the control service module of the dust measuring apparatus is implemented in the controller 2510, the control service module may be implemented in a separate memory, the memory 2540, or an external memory according to some embodiments. The control service module of the dust measuring apparatus may be implemented when the mobile terminal 2000 is shipped or OS/firmware upgrade is performed.

For example, if the user input is a control mode of the dust measuring apparatus, the controller 2510 may establish communication with the dust measuring apparatus. Once communication is established, the controller 2510 may display, on the display unit 2530, a setting window for setting the effective measurement range of the collected dust measuring apparatus. Once the effective measurement range is set in the setting window, the controller 2510 may transmit, to the dust measuring apparatus, a control signal corresponding to the set effective measurement range.

In addition, once communication is established, the controller 2510 may receive the current position information and dust concentration information measured at the current position from the dust measuring apparatus with which communication is established, and include the received current position information and dust concentration information in the setting window.

Subsequently, upon receiving the current position information about the dust measuring apparatus, the controller 2510 may collect environment information about the received current position from an external server, generate guide information for guiding adjustment of the effective measurement range based on the collected environment information, and include the generated guide information in the setting window.

In one embodiment, upon receiving the current position information about the dust measuring apparatus, the controller 2510 may collect environment information about the received current position from the external server, and provide guide information for guiding ventilation based on the collected environment information and the current position information.

In addition, once communication is established, the controller 2510 may receive guide information for guiding adjustment of the effective measurement range from the dust measuring apparatus, and include the received guide information in the setting window.

FIGS. 23 to 28 illustrate a procedure of setting an effective measurement range on a mobile terminal according to an embodiment of the present invention.

Figure 23:
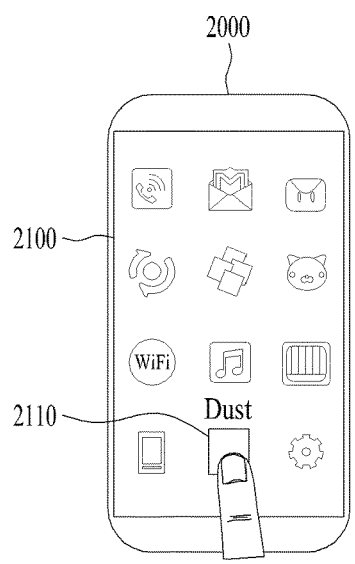
FIGS. 23 to 28 illustrate a procedure of setting an effective measurement range on a mobile terminal according to an embodiment of the present invention.

As shown in FIG. 23, the mobile terminal 2000 may display, on the display screen 2100, the dust measurement control icon 2110 for controlling the dust measuring apparatus.

Then, when the user input for selecting the dust measurement control icon 2110 is received, the mobile terminal 2000 may establish communication with the dust measuring apparatus, recognizing that the user input is in the control mode of the dust measuring apparatus.

Figure 25:
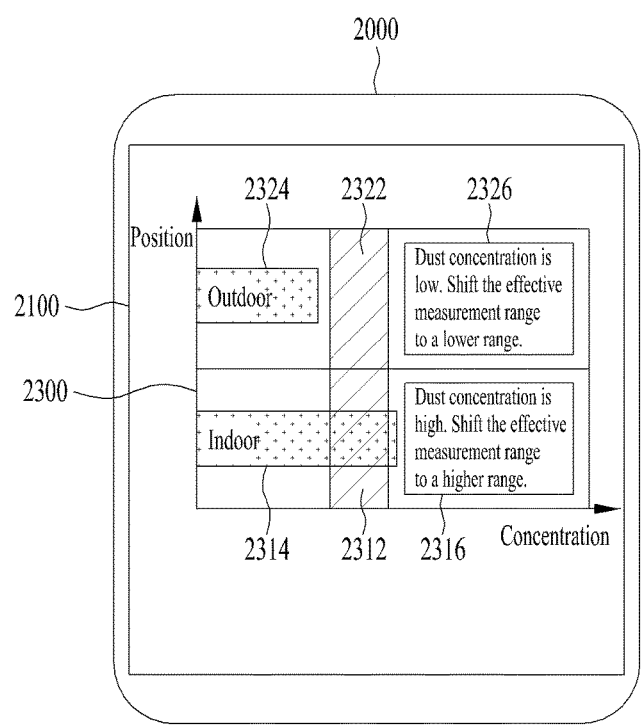

Next, as shown in FIG. 25, once communication is established, the mobile terminal 2000 may display, on the display screen 2100, a setting window for setting an effective measurement range of the dust measuring apparatus.

Figure 24:
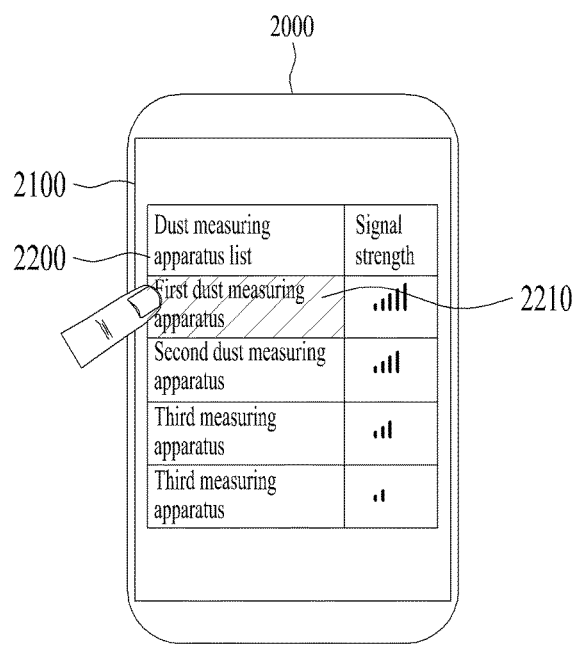

If communication with multiple dust measuring apparatuses is established as shown in FIG. 24, the mobile terminal 2000 may display, on the display screen 2100, a dust measuring apparatus list 2200 including the multiple dust measuring apparatuses with which communication is established. For example, when the mobile terminal 2000 displays the dust measuring apparatus list 2200, the mobile terminal 2000 may arrange the dust measuring apparatuses in descending order of signal strength. When the mobile terminal 2000 is positioned at a first distance d11 from a first dust measuring apparatus, a second distance d12 from a second dust measuring apparatus, a third distance d13 from a third dust measuring apparatus, and a fourth distance d14 from a fourth dust measuring apparatus, signal strength may vary with distance. Accordingly, when the mobile terminal 2000 displays the dust measuring apparatus list 2200, the dust measuring apparatus list 2200 may include the names of the dust measuring apparatuses with which communication is established and corresponding signal strengths.

Subsequently, as shown in FIG. 25, when one dust measuring apparatus is selected in the dust measuring apparatus list 2200, the mobile terminal 2000 may display, on a display screen 2100, a setting window 2300 for setting an effective measurement range of the selected dust measuring apparatus. For example, if the selected dust measuring apparatus is mounted to the interior and exterior of a vehicle, the setting window 2300 may include a dust concentration 2314 in the vehicle, an effective measurement range 2312 within which the dust measuring apparatus in the vehicle may measure the dust concentration, a guide message 2316 for guiding adjustment of the effective measurement range for the dust measuring apparatus in the vehicle, an effective measurement range 2322 within which the dust measuring apparatus outside the vehicle may measure the dust concentration, and a guide message 2326 for guiding adjustment of an effective measurement range for the dust measuring apparatus outside the vehicle.

Herein, the dust concentration 2314 in the vehicle is a high concentration exceeding the maximum value in the effective measurement range 2312 of the indoor dust measuring apparatus, the mobile terminal 2000 may provide the guide message 2316 for guiding shift of the effective measurement range to a higer range since the dust concentration is high and thus it is difficult to perform dust measurement.

In addition, if the dust concentration 2324 outside the vehicle is a low concentration less than the minimum value in the effective measurement range 2322 of the outdoor dust measuring apparatus, the mobile terminal 2000 may provide the guide message 2316 for guiding shift of the effective measurement range to a lower range since the dust concentration is low and thus it is difficult to perform dust measurement.

Figure 26:
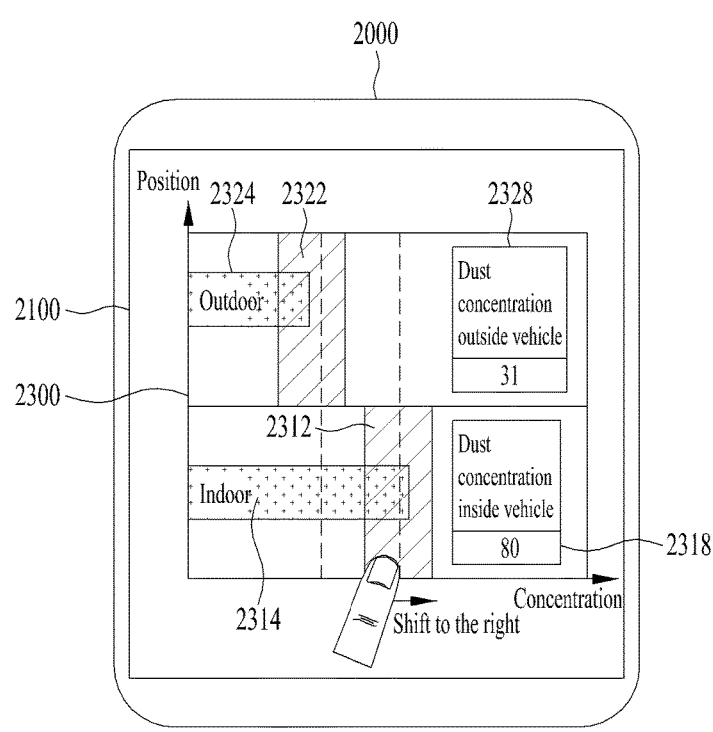

Next, as shown in FIG. 26, when user input for shifting the effective measurement range 2312 of the indoor dust measuring apparatus to a higher range is received, the mobile terminal 2000 may transmit, to the indoor dust measuring apparatus, a control signal for the varied effective measurement range 2312. In addition, the indoor dust measuring apparatus may vary the impedance of a signal corresponding to the varied effective measurement range according to the control signal of the mobile terminal 2000 to perform measurement of high-concentration dust and transmit the measured dust concentration information to the mobile terminal 2000. Subsequently, the mobile terminal 2000 may display, in the setting window 2300, the dust concentration 2318 in the vehicle based on the dust concentration information received from the indoor dust measuring apparatus.

When user input for shifting the effective measurement range 2322 of the outdoor dust measuring apparatus to a lower range is received, the mobile terminal 2000 may transmit, to the outdoor dust measuring apparatus, a control signal for the varied effective measurement range 2322. Then, the outdoor dust measuring apparatus may vary the impedance of a signal corresponding to the varied effective measurement range according to the control signal of the mobile terminal 2000 to perform measurement of low-concentration dust and transmit the measured dust concentration information to the mobile terminal 2000. Subsequently, the mobile terminal 2000 may display, in the setting window 2300, the dust concentration 2328 outside the vehicle based on the dust concentration information received from the outdoor dust measuring apparatus.

In this way, once communication is established, the mobile terminal 2000 may receive the current position information and dust concentration information measured at the current position from the dust measuring apparatus with which communication is established, and include the received current position information and dust concentration information in the setting window 2300.

Once the effective measurement range is set in the setting window 2300, the mobile terminal 2000 may transmit, to the dust measuring apparatus, a control signal corresponding to the set effective measurement range to control the dust measuring apparatus to perform measurement of high-concentration dust or low-concentration dust.

As described above, the dust measuring apparatus according to an embodiment of the present invention may provide user convenience by transmitting, to an external terminal, dust concentration information measured at a current position and guide information for guiding adjustment of the effective measurement range.

In addition, the mobile terminal according to an embodiment of the present invention may provide a setting window for setting the effective measurement range of a dust measuring apparatus to allow the effective measurement range to be manually varied. Thereby, the user may easily and simply control the dust measuring apparatus.

Figure 27:
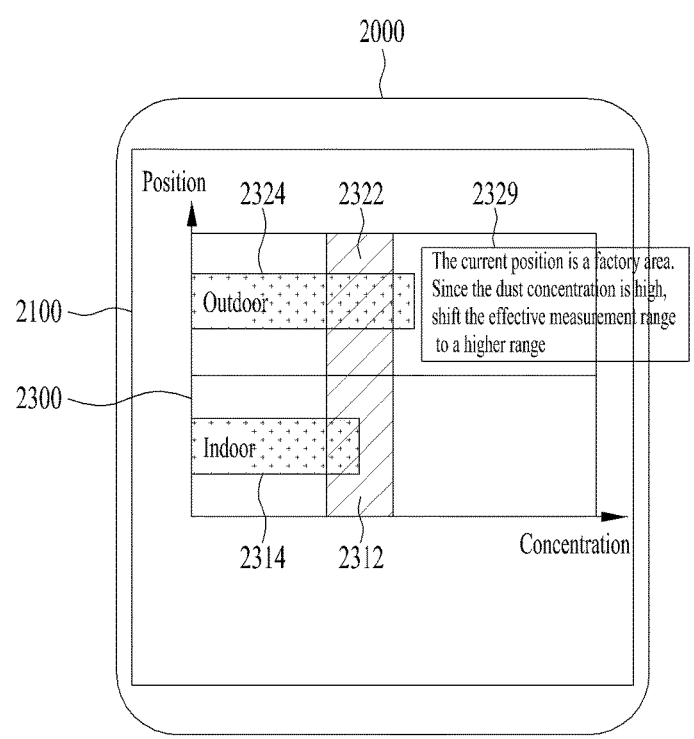

In addition, as shown in FIG. 27, upon receiving the current position information about the outdoor dust measuring apparatus, the mobile terminal 2000 may collect environment information about the received current position from an external server, generate a guide message 2329 for guiding adjustment of the effective measurement range based on the collected environment information, and include the guide information 2329 in the setting window 2300.

For example, when a vehicle passes through a factory area where the dust concentration is high, the mobile terminal 2000 may make a request to an external server for the environment information about the current position based on the current position information about the outdoor dust measuring apparatus of the vehicle. Upon collecting, from the external server, the environment information indicating that the current position is a factory area where the dust concentration is high, the mobile terminal 2000 may generate a guide message 2329 corresponding to the environment information. That is, as the mobile terminal 2000 displays the guide message 2329 for guiding adjustment of the effective measurement range based on the environment information, precision and reliability of dust measurement may be improved.

In one embodiment, the mobile terminal 2000 may collect the environment information about the current position from an external server, and provide guide information for guiding ventilation based on the collected environment information and the current position information. For example, the guide information for guiding ventilation may include a message instructing that the vehicle be ventilated by opening the door, a message for instructing that the air conditioner be turned on, or the like.

By collecting the environment information about the current position of the dust measuring apparatus and providing the guide information for guiding ventilation as described above, the present invention may improve user convenience.

Figure 28:
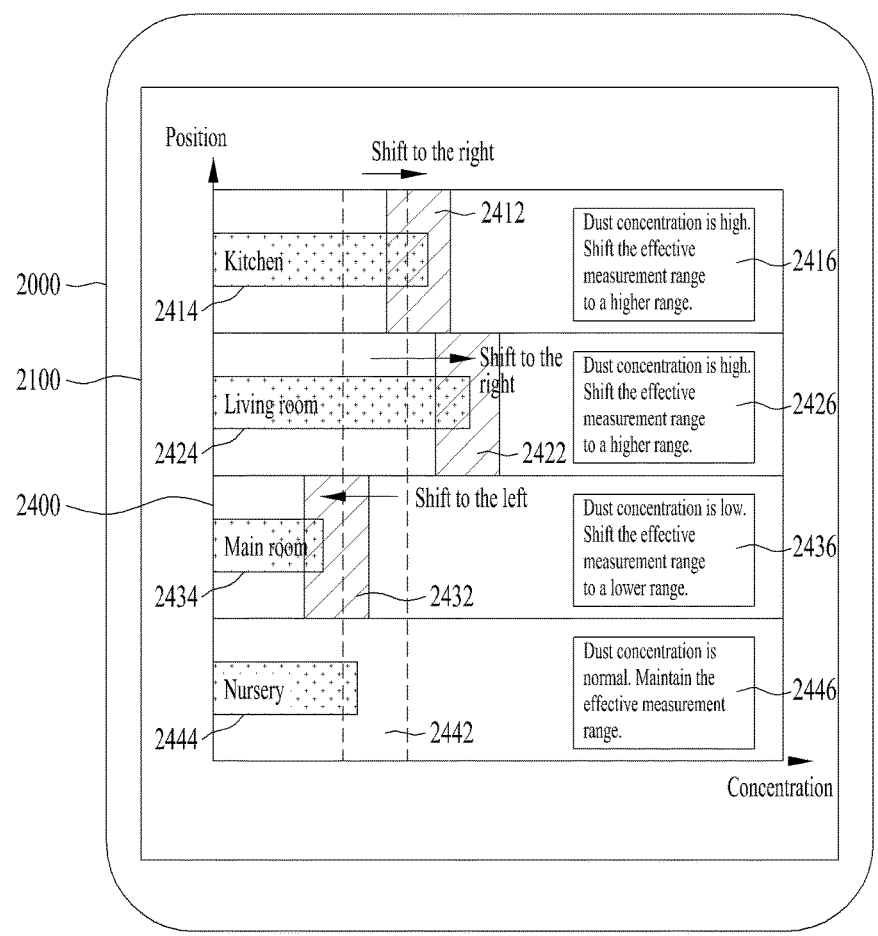

In addition, as shown in FIG. 28, when dust measuring apparatuses are installed in the kitchen, living room, main room and nursery in a household, respectively, the mobile terminal 2000 may include, in a setting window 2400, a dust concentration 2414 in the kitchen, an effective measurement range 2412 in which a dust measuring apparatus for the kitchen is capable of measuring a dust concentration, a guide message 2416 for guiding adjustment of the effective measurement range for the dust measuring apparatus for the kitchen, a dust concentration 2424 in the living room, an effective measurement range 2422 in which a dust measuring apparatus for the living room is capable of measuring a dust concentration, a guide message 2426 for guiding adjustment of the effective measurement range for the dust measuring apparatus for the living room, a dust concentration 2434 in the main room, an effective measurement range 2432 in which a dust measuring apparatus for the main room is capable of measuring a dust concentration, a guide message 2436 for guiding adjustment of the effective measurement range for the dust measuring apparatus for the main room, a dust concentration 2444 in the nursery, an effective measurement range 2442 in which a dust measuring apparatus for the nursery is capable of measuring a dust concentration, and a guide message 2446 for guiding adjustment of the effective measurement range for the dust measuring apparatus for the nursery.

When user input for shifting the effective measurement range of a corresponding dust measuring apparatus to a higher or lower range is received, the mobile terminal 2000 may transmit, to the corresponding dust measuring apparatus, a control signal for the varied effective measurement range, and display an indoor dust concentration in a setting window 2400 based on the dust concentration information received from the corresponding dust measuring apparatus.

Figure 29:
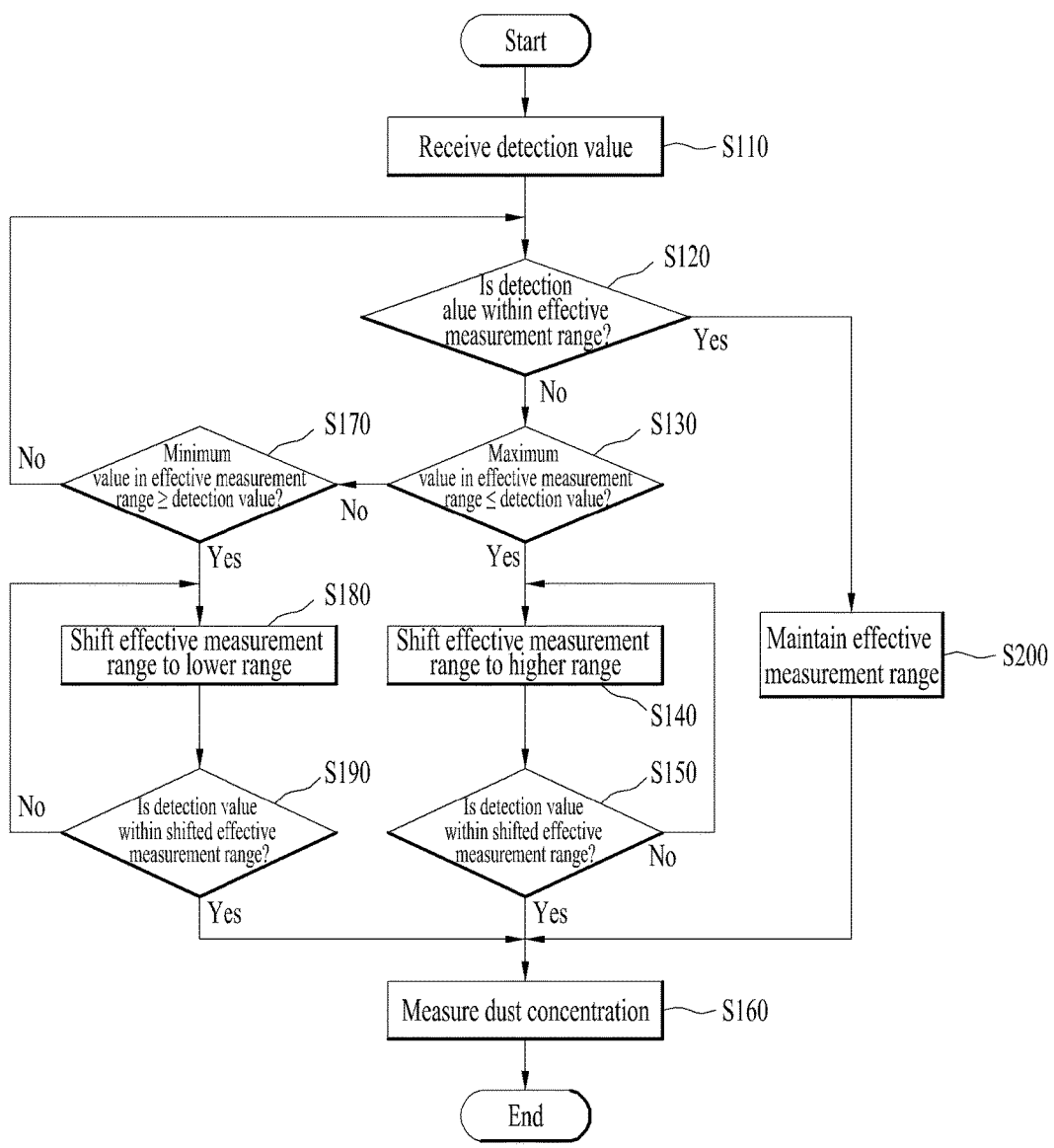
FIG. 29 is a flowchart illustrating a dust measuring method for a dust measuring apparatus according to an embodiment of the present invention.

FIG. 29 is a flowchart illustrating a dust measuring method for a dust measuring apparatus according to an embodiment of the present invention.

As shown in FIG. 29, when a control signal is input, a dust measuring apparatus receives a detection value from a light detector (S810), and checks if the received detection value is within an effective measurement range (S120).

Subsequently, if the detection value is not within the effective measurement range as a result of the checking, the dust measuring apparatus checks if the detection value is greater than or equal to the maximum value in the effective measurement range (S130).

Next, if the detection value is greater than or equal to the maximum value in the effective measurement range as a result of the checking, the dust measuring apparatus increases the maximum value and minimum value in the effective measurement range by decreasing the impedance of a signal received from the light detector (S140).

Then, the dust measuring apparatus checks if the detection value is within the shifted effective measurement range (S150).

Subsequently, if the detection value is within the shifted effective measurement range as a result of the checking, the dust measuring apparatus measures a dust concentration (S160).

In addition, if the detection value is not a value greater than or equal to the maximum value in the effective measurement range as a result of checking if the detection value is greater than or equal to the maximum value (S130), the dust measuring apparatus checks if the detection value is less than or equal to the minimum value in the effective measurement range (S170).

Next, if the detection value is less than or equal to the minimum value in the effective measurement range as a result of the checking the dust measuring apparatus decreases the maximum value and minimum value in the effective measurement range by increasing the impedance of a signal received from the light detector (S180).

Then, the dust measuring apparatus checks if the detection value is within the shifted effective measurement range (S190).

Subsequently, if the detection value is within the shifted effective measurement range as a result of the checking, the dust measuring apparatus measures a dust concentration (S160).

If the detection value is within the effective measurement range as a result of checking if the received detection value is within the effective measurement range (S120), the dust measuring apparatus maintains the effective measurement range without varying the impedance of a signal received from the light detector (S200), and then measures a dust concentration (S160).

In one embodiment, if communication with an external terminal is established, the dust measuring apparatus may transmit, to the external terminal, the current position information about the dust measuring apparatus and dust concentration information measured at the current position.

In another embodiment, if communication with an external terminal is established, the dust measuring apparatus may transmit, to the external terminal, guide information for guiding adjustment of the effective measurement range.

As described above, according to an embodiment of the present invention, the measurement range of dust concentrations may be widened by varying the effective measurement range within which dust measurement is possible.

Figure 30:
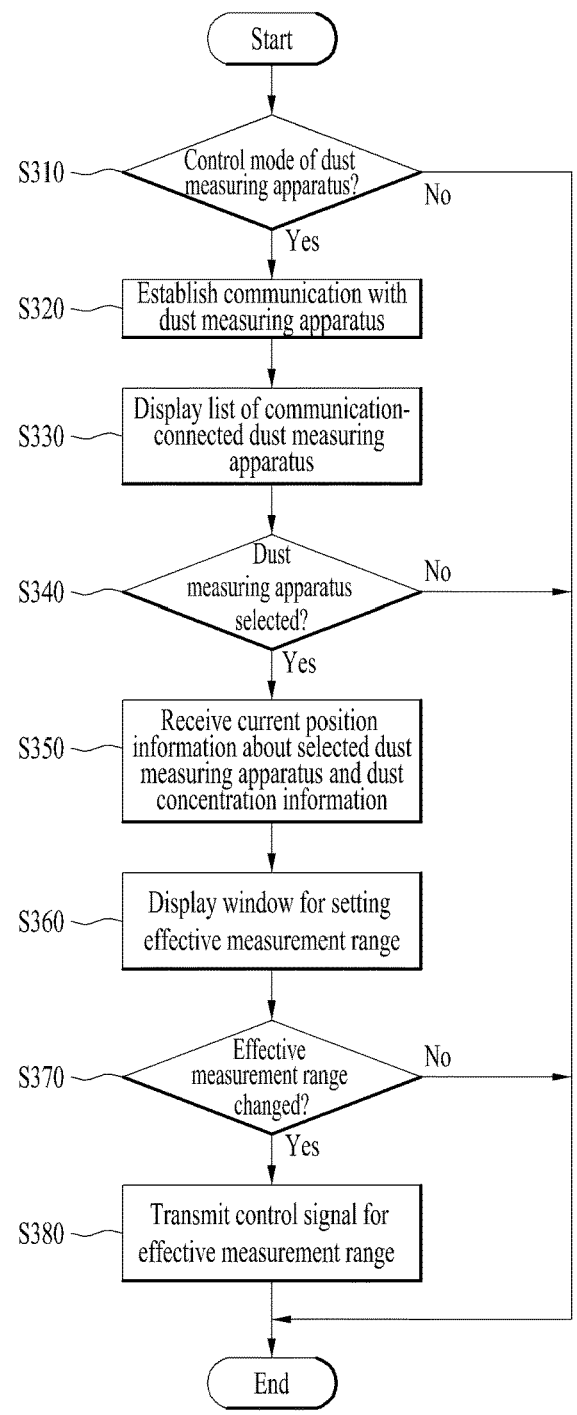
FIG. 30 is a flowchart illustrating a method for controlling a dust measuring apparatus in a mobile terminal according to an embodiment of the present invention.

FIG. 30 is a flowchart illustrating a method for controlling a dust measuring apparatus in a mobile terminal according to an embodiment of the present invention.

As shown in FIG. 30, the mobile terminal checks if the user input is the control mode of a dust measuring apparatus (S310).

Subsequently, if the user input is the control mode of a dust measuring apparatus as a result of the checking, the mobile terminal establishes communication with the dust measuring apparatus (S320).

Next, the mobile terminal displays, on the display screen, a list of dust measuring apparatuses with which communication is established (S330). Herein, if there are multiple dust measuring apparatuses with which communication is established, the mobile terminal may arrange the dust measuring apparatuses in descending order of signal strength.

Then, the mobile terminal checks if user input for selecting a dust measuring apparatus in the dust measuring apparatus list is received (S340).

Subsequently, the mobile terminal receives, from the selected dust measuring apparatus, the current position information and dust concentration information measured at the current position (S350).

Next, the mobile terminal displays, on the display screen, an effective measurement range setting window including the received current position information and dust concentration information (S360).

In one embodiment, upon receiving the current position information about the dust measuring apparatus, the mobile terminal may collect environment information about the received current position from an external server, generate guide information for guiding adjustment of the effective measurement range based on the collected environment information, and display the generated guide information in the setting window.

In another embodiment, upon receiving the current position information about the dust measuring apparatus, the mobile terminal may collect environment information about the received current position from an external server, generate guide information for guiding ventilation based on the collected environment information and the current position information, and display the guide information in the setting window.

In another embodiment, once communication is established, the mobile terminal may receive guide information for guiding adjustment of the effective measurement range from the dust measuring apparatus with which communication is established, and display the received guide information in the setting window.

Next, the mobile terminal checks if user input for varying the effective measurement range is provided through the effective measurement range setting window (S370).

Then, if the effective measurement range is varied, the mobile terminal may transmit, to the dust measuring apparatus, a control signal corresponding to the varied effective measurement range (S380).

Subsequently, when dust concentration information corresponding to the varied effective measurement range is received from the dust measuring apparatus, the mobile terminal may display the received dust concentration information on the display screen.

In one embodiment, upon receiving the current position information about the dust measuring apparatus, the mobile terminal may collect environment information about the received current position from an external server, generate guide information for guiding adjustment of the effective measurement range based on the collected environment information, and display the generated guide information in the setting window.

In another embodiment, upon receiving the current position information about the dust measuring apparatus, the mobile terminal may collect environment information about the received current position from the external server, generate guide information for guiding ventilation based on the collected environment information and the current position information, and display the guide information in the setting window.

As described above, the mobile terminal according to an embodiment of the present invention may provide a setting window for setting the effective measurement range of a dust measuring apparatus to allow the effective measurement range to be manually varied. Thereby, the user may easily and simply control the dust measuring apparatus.

As described above, according to an embodiment of the present invention, the measurement range of dust concentrations may be widened by varying the effective measurement range within which dust measurement is possible.

In addition, according to an embodiment of the present invention, in varying the effective measurement range, the impedance of a signal received from the light detector is varied. Thereby, circuit configuration may be simplified.

In addition, according to an embodiment of the present invention, measurement precision may be enhanced by varying the effective measurement range according to a plurality of preset variation levels.

In addition, according to an embodiment of the present invention, a high-concentration measurement range and a low-concentration measurement range which are adjacent to the effective measurement range are configured to partially overlap the effective measurement range. Thereby, reliability of dust concentration measurement may be enhanced.

In addition, according to an embodiment of the present invention, the effective measurement range may be widened or narrowed according to an amplification rate of a signal received from the light detector. Thereby, the measurement range of dust concentrations may be widened.

In addition, according to an embodiment of the present invention, the effective measurement range is readjusted according to the detection range performance of the light detector. Thereby, measurement precision may be enhanced.

In addition, according to an embodiment of the present invention, user convenience may be provided by transmitting, to an external terminal, dust concentration information measured at a current position and guide information for guiding adjustment of the effective measurement range.

In addition, according to an embodiment of the present invention, the effective measurement range may be manually varied by providing a setting window for setting the effective measurement range of a dust measuring apparatus. Thereby, the user may easily and simply control the dust measuring apparatus.

Further, according to an embodiment of the present invention, guide information for guiding ventilation is provided by collecting environment information about a current position of the dust measuring apparatus. Thereby, user convenience may be improved.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:
1. A dust measuring apparatus comprising:
 a flow channel defining unit for defining a flow channel allowing a fluid containing dust to move through;
 a light emitter for emitting light into the flow channel;
 a light detector for detecting light scattered from the dust in the flow channel and converting the same into an electrical signal; and
 a controller for controlling the flow channel defining unit, the light emitter and the light detector,
 wherein the controller is configured to:
  verify whether a detection value received from the light detector is within an effective measurement range;
  vary the effective measurement range by varying an impedance of a signal received from the light detector when the detection value is outside the effective measurement range; and
  measure, when the detection value is within the varied effective measurement range, a dust concentration based on the detection value without varying an impedance of a signal received from the light detector.

2. The dust measuring apparatus according to claim 1, wherein, when the controller varies the effective measurement range,
 the controller is further configured to increase a maximum value and minimum value in the effective measurement range if the detection value is greater than or equal to the maximum value in the effective measurement range, and decreases the maximum value and minimum value in the effective measurement range if the detection value is less than or equal to the minimum value in the effective measurement range.

3. The dust measuring apparatus according to claim 2, wherein the controller is further configured to:
decrease an impedance of a signal received from the light detector to increase the maximum value and minimum value in the effective measurement range; and
increase the impedance of the signal received from the light detector to decrease the maximum value and minimum value the effective measurement range.

4. The dust measuring apparatus according to claim 1, wherein the controller is further configured to vary the effective measurement range according to preset variation levels.

5. The dust measuring apparatus according to claim 1, wherein the controller comprises:
a measurement range adjuster for adjusting the effective measurement range according to the detection value received from the light detector.

6. The dust measuring apparatus according to claim 1, wherein the controller widens or narrows the effective measurement range according to an amplification rate of a signal received from the light detector.

7. The dust measuring apparatus according to claim 6, wherein the controller is further configured to:
widen, if the amplification rate of the signal received from the light detector increases, the effective measurement range by increasing a maximum value in the effective measurement range and decreasing a minimum value in the effective measurement range; and
narrow, if the amplification rate of the signal received from the light detector decreases, the effective measurement range by decreasing the maximum value in the effective measurement range and increasing the minimum value in the effective measurement range.

8. The dust measuring apparatus according to claim 1, wherein the light detector comprises:
a first detector for detecting light scattered within a first detection range in a light emission region of the flow channel; and
a second detector for detecting light scattered within a second detection range in the light emission region of the flow channel, the second detection range being narrower than the first detection range.

9. The dust measuring apparatus according to claim 8, wherein the first detector comprises a first lens having a first angle of view,
wherein the second detector comprises a second lens having a second angle of view, the second angle of view being narrower than the first angle of view.

10. The dust measuring apparatus according to claim 8, wherein the controller is configured to:
check, when a first detection value is received from the first detector, if the first detection value is within a first effective measurement range; and
check, when a second detection value is received from the second detector, if the second detection value is within a second effective measurement range.

11. The dust measuring apparatus according to claim 10, wherein a maximum value in the second effective measurement range is greater than a maximum value in the first effective measurement range,
wherein a minimum value in the second effective measurement range is greater than a minimum value in the first effective measurement range.

12. The dust measuring apparatus according to claim 1, further comprising:
a communication unit for establishing communication with an external terminal,
wherein the controller is further configured to:
transmit, when the communication with the external terminal is established, information about the measured dust concentration to the external terminal; and
vary, when a control signal is received from the external terminal, the effective measurement range according to the received control signal, measure a dust concentration based on the varied effective measurement range, and transmit information about the measured dust concentration to the external terminal.

13. The dust measuring apparatus according to claim 12, wherein, when the controller transmits the information about the dust concentration, the controller provides the external terminal with guide information for guiding adjustment of the effective measurement range.

14. The dust measuring apparatus according to claim 12, further comprising:
a sensing unit for sensing a current position,
wherein, when the communication with the external terminal is established, the controller transmits, to the external terminal, information about the current position and information about a dust concentration measured at the current position.

15. A mobile terminal for controlling a dust measuring apparatus for varying an effective measurement range enabling measurement of dust concentrations, the mobile terminal comprising:
an input unit;
a communication unit for establishing communication with the dust measuring apparatus;
a display unit for displaying a setting window for setting an effective measurement range for the dust measuring apparatus; and
a controller for controlling the input unit, the communication unit and the display unit,
wherein the controller is configured to:
establish the communication with the dust measuring apparatus when a user input is a control mode of the dust measuring apparatus;
display, when the communication is established, a setting window for setting the effective measurement range for the communication-connected dust measuring apparatus, wherein the setting window contains guide information to guide an adjustment of the effective measurement range; and
transmit, when the effective measurement range is set in the setting window, a control signal corresponding to the set effective measurement range to the dust measuring apparatus.

16. The mobile terminal according to claim 15, wherein the controller is configured to:
receive, when the communication is established, information about a current position and information about a dust concentration measured at the current position from the communication-connected dust measuring apparatus; and
include, in the setting window, the received information about the current position and the dust concentration.

17. The mobile terminal according to claim 16, wherein the controller is further configured to:
collect, when the information about the current position of the dust measuring apparatus is received, environment information about the received current position from an external server; and generate guide information for guiding adjustment of the effective measurement range based on the collected environment information and include the same in the setting window.

18. The mobile terminal according to claim 16, wherein the controller is configured to:
collect, when the information about the current position of the dust measuring apparatus is received, environment information about the received current position from an external server; and
generate guide information for guiding ventilation based on the collected environment information and the information about the current position and include the same in the setting window.

19. The mobile terminal according to claim 15, wherein the controller is configured to:
receive, when the communication is established, the guide information from the communication-connected dust measuring apparatus; and
include and display the received guide information in the setting window.

* * * * *